(12) United States Patent
Shinkai et al.

(10) Patent No.: US 6,204,277 B1
(45) Date of Patent: Mar. 20, 2001

(54) PROPIONIC ACID DERIVATIVES AND APPLICATIONS THEREOF

(75) Inventors: Hisashi Shinkai; Tsutomu Shibata; Satoshi Ohrui, all of Takatsuki (JP)

(73) Assignee: Japan Tobacco Inc., Tokyo (JP)

(*) Notice: Subject to any disclaimer, the term of this patent is extended or adjusted under 35 U.S.C. 154(b) by 0 days.

(21) Appl. No.: 09/242,620

(22) PCT Filed: Aug. 19, 1997

(86) PCT No.: PCT/JP97/02873

§ 371 Date: May 3, 1999

§ 102(e) Date: May 3, 1999

(87) PCT Pub. No.: WO98/07699

PCT Pub. Date: Feb. 26, 1998

(30) Foreign Application Priority Data

Aug. 19, 1996 (JP) .................................... 8-217548

(51) Int. Cl.⁷ .................. A61K 31/421; A61K 31/44; A61K 31/422; C07D 213/30; C07D 263/32
(52) U.S. Cl. .................. 514/374; 514/277; 546/339; 548/236
(58) Field of Search ............... 548/236; 546/339; 514/277, 374

(56) References Cited

U.S. PATENT DOCUMENTS

| | | |
|---|---|---|
| 4,725,610 | 2/1988 | Meguro et al. . |
| 5,089,514 | 2/1992 | Hulin . |
| 5,306,726 | 4/1994 | Hulin . |
| 5,334,604 | 8/1994 | Goldstein et al. . |
| 5,498,621 | 3/1996 | Dow et al. . |
| 5,591,862 | 1/1997 | Sohda et al. . |
| 5,665,748 | 9/1997 | Sohda et al. . |
| 5,728,720 | 3/1998 | Shinkai . |

FOREIGN PATENT DOCUMENTS

| | | |
|---|---|---|
| 0 684 242 | 11/1995 | (EP) . |
| 97 31907 | 9/1987 | (WO) . |
| 9 413 650 | 6/1994 | (WO) . |
| 94 13650 | 6/1994 | (WO) . |
| 9 638 415 | 12/1996 | (WO) . |
| 98 00137 | 1/1998 | (WO) . |

OTHER PUBLICATIONS

Shinkai, CA 123:340099, 1995.*
Takeno et al., CA 126:89361, 1997.*
B.C.C. Cantello et al. Journal of Medicinal Chemistry, vol. 37, No. 23, "Omega (Heterocyclylamino)Alkoxybenzyl–2, 4–Thiazolidinediones as Potent Antihyperglycemic Agents," pp. 3977–3895, Jan. 1, 1994.

* cited by examiner

Primary Examiner—Laura L. Stockton
(74) Attorney, Agent, or Firm—Foley & Lardner

(57) ABSTRACT

A novel propionic acid derivative of the formula (I):

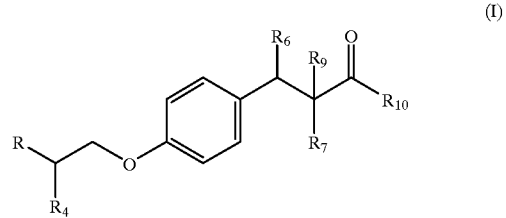

and a pharmaceutically acceptable salt thereof, and pharmaceutical compositions containing the derivative. The propionic acid derivative and a pharmaceutically acceptable salt thereof have superior hypoglycemic action and are expected to show hypolipidemic action and to be useful as therapeutic agents for diabetes and complications of diabetes, as well as related diseases such as hyperlipemia.

7 Claims, No Drawings

PROPIONIC ACID DERIVATIVES AND APPLICATIONS THEREOF

This application is a 371 of PCT/JP97/02873 filed Aug. 19, 1997.

TECHINCAL FIELD

The present invention relates to novel propionic acid derivatives. More particularly, the present invention relates to novel propionic acid derivatives and pharmaceutical compositions containing said derivatives, which have hypoglycemic action, which are expected to have hypolipidemic action, and which are useful as therapeutic agents of diabetes mellitus and complications thereof, diabetes-related diseases such as hyperlipemia, and the like.

BACKGROUND ART

In general, the treatment of non-insulin-dependent diabetes mellitus (NIDDM) involves a combination of alimentotherapy, kinesitherapy, and administration of insulin or orally active hypoglycemic agents. As the oral hypoglycemic agents, there are currently known sulfonylureas such as tolbutamide, chlorpropamide, acetohexamide, glibenclamide and tolazamide, and biguanides such as phenformin, buformin and metformin.

While the sulfonylureas have strong hypoglycemic action, they sometimes induce severe and prolonged hypoglycemia, and chronic use thereof may impair their effectiveness. In addition, the biguanides frequently induce severe lactic acidosis. For these reasons, the use of these medications has required considerable amount of attention.

Meanwhile, Japanese Patent Unexamined Publication No. 85372/1986 discloses that thiazolidinedione derivatives, such as 5-[4-[2-(5-methyl-2-phenyl-4-oxazolyl)ethoxy]benzyl]-2,4-thiazolidinedione, have hypoglycemic action.

Japanese Patent Unexamined Publication No. 170478/1991 teaches that oxazolidinedione derivatives, such as 5-[4-[2-(2-phenyl-5-methyloxazol-4-yl)ethoxy]benzyl]-2,4-oxazolidinedione, have hypoglycemic action and hypocholesterolemic action, and Japanese Patent Unexamined Publication No. 165735/1995 teaches that oxazolidinedione derivatives, such as 5-[3-[4-[(2-benzo[b]thien-2-yl-5-methyl-4-oxazolyl)methoxy]phenyl]propyl]- 2,4-oxazolidinedione, also have hypoglycemic action and hypocholesterolemic action.

Japanese Patent Application under PCT laid-open under Kohyo No. 5-507920 discloses that 3-aryl-2-hydroxypropionic acid derivatives, such as α-methoxy-4-[2-(5-methyl-2-phenyl-4-phenyl-4-oxazolyl)ethoxy]benzenepropanic acid and ethyl α-acetylthio-4-[2-(5-methyl-2-phenyl-4-oxazolyl)ethoxy]benzenepropionate, have hypoglycemic action. This publication also recites ethyl α-hydroxy-4-[2-(5-methyl-2-phenyl-4-oxazolyl)ethoxy]benzenepropanate as an intermediate compound. In addition, Japanese Patent Application under PCT laid-open under Kohyo No. 5-508654 discloses that hydroxyurea derivatives, such as N-[(methoxycarbonyl)oxy]-N-[[4-[2-(5-methyl-2-phenyl-4-oxazolyl)ethoxy]phenyl]methyl]urea, have hypoglycemic action.

WO95/18125 discloses that isoxazolidinedione derivatives, such as 4-[4-[2-(2-phenyl-5-methyl-4-oxazolyl)ethoxy]benzyl]-3,5-isoxazolidinedione, have hypoglycemic action.

WO94/13650 discloses that dimethyl 2-[4-[2-[N-(2-benzooxazolyl)-N-methylamino]ethoxy]phenylmethyl]propane-1,3-dioate and dimethyl 2-[4-[2-[N-(2-benzooxazolyl)-N-methylamino]ethoxy]phenylmethylene]propane-1,3-dioate have hypoglycemic action.

Japanese Patent Unexamined Publication No. 53555/1995 recites ethyl 4-[2-(5-methyl-2-phenyl-4-oxazolyl)ethoxy]cinnamate as an intermediate compound.

Japanese Patent Unexamined Publication No. 101945/1995 describes ethyl (E)-4-[2-(5-ethyl-2-pyridyl)ethoxy]cinnamate as a reference compound.

The above-mentioned compounds do not necessarily show satisfactory activities. Rather, the use of these compounds gives rise to concerns about the side effects such as toxicity. Moreover, the above-mentioned literatures do not suggest a propionic acid derivative such as the compounds of the present invention.

Further, WO95/18125 discloses diesters of malonic acid, such as dimethyl 4-[2-(2-phenyl-5-methyl-4-oxazolyl)ethoxy]benzilidenemalonate, as an intermediate compound for isoxazolidinedione derivatives such as 4-[4-[2-(2-phenyl-5-methyl-4-oxazolyl)ethoxy]benzyl]-3,5-isoxazolidinedione. Nevertheless, it does not suggest that such diesters of malonic acid have hypoglycemic action, much less gives any data suggesting the hypoglycemic action.

DISCLOSURE OF THE INVENTION

The present inventors have conducted intensive studies in an attempt to provide a compound useful for the treatment of diabetes mellitus, its complications and hyperlipemia, and found a novel propionic acid derivative which is low toxic and has superior hypoglycemic action and hypolipidemic action, which resulted in the completion of the present invention.

Accordingly, the present invention provides pharmaceutical compositions inclusive of the novel propionic acid derivatives of the following (1) to (3), and pharmaceutical compositions such as the therapeutic agents of diabetes mellitus of the following (4) to (7).

(1) A novel propionic acid derivative of the formula (I):

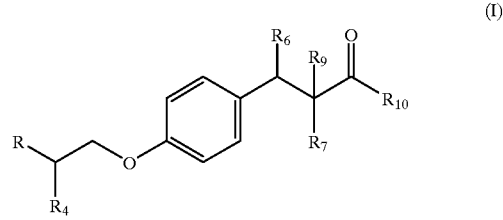

wherein R is a group of the formula:

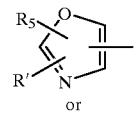

or

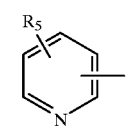

wherein
R' is an optionally substituted aromatic hydrocarbon, an optionally substituted alicyclic hydrocarbon, an optionally substituted heterocyclic group or an optionally substituted fused heterocyclic group, and $R_5$ is a lower alkyl;

$R_4$ is a hydrogen atom or a lower alkyl;

$R_6$ is a hydrogen atom or forms, together with $R_9$, a double bond;

$R_7$ is a carboxy, an acyl, an optionally substituted alkoxycarbonyl, an optionally substituted lower alkyl, an optionally substituted carbamoyl, an optionally substituted aryloxycarbonyl, an optionally substituted aralkyloxycarbonyl or a group of the formula —Y—$R_8$ wherein Y is —NH— or an oxygen atom and $R_8$ is an optionally substituted acyl or an optionally substituted alkoxycarbonyl;

$R_9$ is a hydrogen atom, an optionally substituted lower alkyl or an optionally substituted lower alkoxycarbonyl; and $R_{10}$ is a hydroxy, an optionally substituted amino, an optionally substituted lower alkoxy, an optionally substituted lower alkyl, an optionally substituted aryloxy or an optionally substituted aralkyloxy, provided that when $R_7$ is an alkoxycarbonyl and $R_9$ is a hydrogen atom, $R_{10}$ is not a lower alkoxy, and a pharmaceutically acceptable salt thereof.

(2) The novel propionic acid derivative of (1) above, having the formula (I):

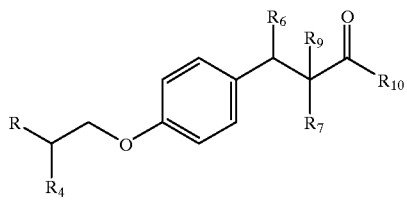

wherein
R is a group of the formula

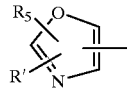

wherein
R' is an aromatic hydrocarbon or a fused heterocyclic group, and
$R_5$ is a lower alkyl;

$R_4$ is a hydrogen atom;

$R_6$ is a hydrogen atom;

$R_7$ is a carboxy, an acyl, an alkoxycarbonyl, a lower alkyl substituted by alkoxycarbonyl, a lower alkyl, a carbamoyl, a carbamoyl optionally substituted by alkoxyalkyl or acyl, an aryloxycarbonyl, an aralkyloxycarbonyl or a group of the formula —Y—$R_8$ wherein Y is —NH— or an oxygen atom and $R_8$ is an acyl or an alkoxycarbonyl;

$R_9$ is a hydrogen atom or a lower alkyl optionally substituted by alkoxycarbonyl; and $R_{10}$ is a hydroxy, an amino optionally substituted by lower alkyl, a lower alkoxy, a lower alkyl, an aryloxy or an aralkyloxy, provided that when $R_7$ is an alkoxycarbonyl and $R_9$ is a hydrogen atom, $R_{10}$ is not a lower alkoxy, and a pharmaceutically acceptable salt thereof.

(3) The novel propionic acid derivative of (1) or (2) above, which is a member selected from the group consisting of:

2-methoxycarbonyl-3-[4-[2-(5-methyl-2-phenyl-4-oxazolyl)ethoxy]phenyl]propionic acid, methyl 2-carbamoyl-3-[4-[2-(5-methyl-2-phenyl-4-oxazolyl)ethoxy]phenyl]propionate, 2-[4-[2-(5-methyl-2-phenyl-4-oxazolyl)ethoxy]benzyl] malonic acid, methyl 2-methoxycarbonylcarbamoyl-3-[4-[2-(5-methyl-2-phenyl-4-oxazolyl)ethoxy]phenyl]propionate, 2-methoxycarbonyl-2-methyl-3-[4-[2-(5-methyl-2-phenyl-4-oxazolyl)ethoxy]phenyl]propionic acid, methyl 2-carbamoyl-2-methyl-3-[4-[2-(5-methyl-2-phenyl-4-oxazolyl)ethoxy]phenyl]propionate, 2-carbamoyl-2-methyl-3-[4-[2-(5-methyl-2-phenyl-4-oxazolyl)ethoxy]phenyl]propionic acid and 2-benzyloxycarbonyl 3-[4-[2-(5-methyl-2-phenyl-4-oxazolyl)ethoxy]phenyl]propionic acid, and a pharmaceutically acceptable salt thereof.

(4) A pharmaceutical composition comprising a propionic acid derivative of the formula (I'):

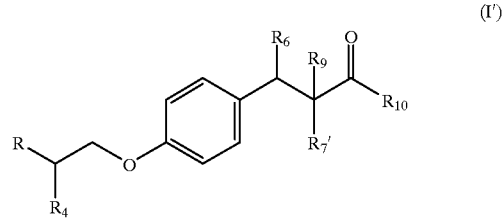

wherein R is a group of the formula:

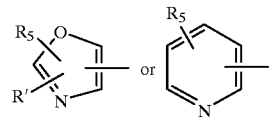

wherein
R' is an optionally substituted aromatic hydrocarbon, an optionally substituted alicyclic hydrocarbon, an optionally substituted heterocyclic group or an optionally substituted fused heterocyclic group, and
$R_5$ is a lower alkyl;

$R_4$ is a hydrogen atom or a lower alkyl;

$R_6$ is a hydrogen atom or forms, together with $R_9$, a double bond;

$R_7'$ is a hydrogen atom, a hydroxy, a carboxy, an acyl, an optionally substituted alkoxycarbonyl, an optionally substituted lower alkyl, an optionally substituted carbamoyl, an optionally substituted aryloxycarbonyl, an optionally substituted aralkyloxycarbonyl or a group of the formula —Y—$R_8$ wherein Y is —NH— or an oxygen atom and $R_8$ is an optionally substituted acyl, or an optionally substituted alkoxycarbonyl, an aryloxycarbonyl or an aralkyloxycarbonyl;

$R_9$ is a hydrogen atom, an optionally substituted lower alkyl or an optionally substituted lower alkoxycarbonyl; and $R_{10}$ is a hydroxy, an optionally substituted amino, an optionally substituted lower alkoxy, an optionally substituted lower alkyl, an optionally substituted aryloxy or an optionally substituted aralkyloxy, and a pharmaceutically acceptable salt thereof.

(5) The pharmaceutical composition of (4) above, comprising a propionic acid derivative of the formula (I'):

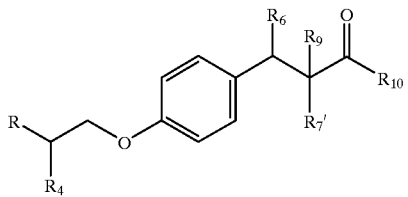

wherein R is a group of the formula:

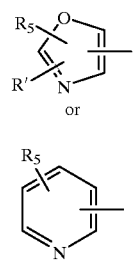

or

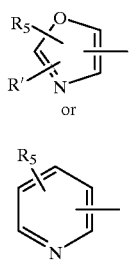

wherein
R' is an aromatic hydrocarbon, or a fused heterocyclic group, and
$R_5$ is a lower alkyl;
$R_4$ is a hydrogen atom;
$R_6$ is a hydrogen atom;
$R_7'$ is a hydrogen atom, a hydroxy, a carboxy, an acyl, an alkoxycarbonyl, a lower alkyl substituted by alkoxycarbonyl, a lower alkyl, a carbamoyl, a carbamoyl optionally substituted by alkoxyalkyl or acyl, an aryloxycarbonyl, an aralkyloxycarbonyl or a group of the formula —Y—$R_8$ wherein Y is —NH— or an oxygen atom and $R_8$ is an acyl, an alkoxycarbonyl, an aryloxycarbonyl or an aralkyloxycarbonyl;
$R_9$ is a hydrogen atom or a lower alkyl optionally substituted by alkoxycarbonyl; and
$R_{10}$ is a hydroxy, a lower alkyl, a carbamoyl, an alkoxycarbonyl, an amino optionally substituted by acyl or lower alkylthiocarbonyl, a lower alkoxy, an aryloxy or an aralkyloxy,
and a pharmaceutically acceptable salt thereof.

(6) The pharmaceutical composition of (4) or (5) above, comprising a propionic acid derivative which is a member selected from the group consisting of:
2-methoxycarbonyl-3-[4-[2-(5-methyl-2-phenyl-4-oxazolyl)ethoxy]phenyl]propionic acid,
methyl 2-carbamoyl-3-[4-[2-(5-methyl-2-phenyl-4-oxazolyl)ethoxy]phenyl]propionate,
2-[4-[2-(5-methyl-2-phenyl-4-oxazolyl)ethoxy]benzyl]malonic acid,
methyl 2-methoxycarbonylcarbamoyl-3-[4-[2-(5-methyl-2-phenyl-4-oxazolyl)ethoxy]phenyl]propionate,
N-[3-[4-[2-(2-(benzothiophen-2-yl)-5-methyl-4-oxazolyl)ethoxy]phenyl]propionyl]urea,
methyl 3-[4-[2-(5-methyl-2-phenyl-4-oxazolyl)ethoxy]phenyl]propionate, 3-[4-[2-(5-methyl-2-phenyl-4-oxazolyl)ethoxy]phenyl]propionamide,
methyl N-[3-[4-[2-(5-methyl-2-phenyl-4-oxazolyl)ethoxy]phenyl]propionyl]carbamate,
S-methyl-3-[4-[2-(5-methyl-2-phenyl-4-oxazolyl)ethoxy]phenyl]propionyl]thiocarbamate,
2-carbamoyl-2-methyl-3-[4-[2-(5-methyl-2-phenyl-4-oxazolyl)ethoxy]phenyl]propionic acid,
tert-butylmethyl 2-[4-[2-(5-methyl-2-phenyl-4-oxazolyl)ethoxy]benzylidene]malonate,
tert-butylmethyl 2-[4-[2-(5-methyl-2-phenyl-4-oxazolyl)ethoxy]benzyl]malonate and
diethyl 4-[2-(5-methyl-2-phenyl-4-oxazolyl)ethoxy]benzylmalonate,
and a pharmaceutically acceptable salt thereof.

(7) The pharmaceutical composition of any one of (4) to (6) above, which is a therapeutic agent of diabetes.

Each symbol used in the present specification is defined as follows.

The aromatic hydrocarbon is exemplified by aralkyl such as phenyl, biphenyl, naphthyl and benzyl, with preference given to phenyl and benzyl, and particular preference given to phenyl.

The alicyclic hydrocarbon is exemplified by alicyclic hydrocarbon having 3 to 7 carbon atoms, such as cyclopropyl, cyclobutyl, cyclopentyl, cyclohexyl, cycloheptyl, cyclopropenyl, cyclobutenyl, cyclobutadienyl, cyclopentenyl, cyclopentadienyl, cyclohexenyl, cyclohexadiethyl, cycloheptenyl, cycloheptadienyl and the like, with preference given to cyclopropyl, cyclobutyl, cyclopentyl and cyclohexyl.

Examples of the heterocyclic group include 5 or 6-membered heterocycle and aromatic heterocycle, both of which having, besides the carbon atom, 1 to 3 hetero atom(s) which is(are) selected from nitrogen atom, oxygen atom and sulfur atom, as the atom constituting the ring. Examples thereof include thienyl, furyl, pyrrolyl, imidazolyl, pyrazolyl, thiazolyl, isothiazolyl, oxazolyl, isooxazolyl, oxadiazolyl, thiadiazolyl, triazolyl, pyridyl, pyrazinyl, pyrimidinyl, pyridazinyl, triadinyl, dithiazolyl, dioxoranyl, dithiolyl, pyrrolidinyl, dithiadiazinyl, thiaziadinyl, morpholinyl, oxadinyl, thiazinyl, pyperadinyl, piperidinyl, pyranyl, thiopyranyl and the like, with preference given to pyridnyl, pyrazinyl and pyrimidinyl.

Examples of the fused heterocyclic group include a ring wherein 5 or 6-membered heterocycles or aromatic heterocycles are fused, and a ring wherein these heterocycles are fused with 4 to 6-membered aromatic hydrocarbon ring, all of which having, besides the carbon atom, 1 to 3 hetero atom(s) which is(are) selected from nitrogen atom, oxygen atom and sulfur atom, as the atom constituting the ring. Examples thereof include furoisoxazolyl, imidazothiazolyl, thienoisothiazolyl, thienothiazolyl, thienothiazolyl, imidazopyrazolyl, cyclopentapyrazolyl, pyrrolopyrolyl, cyclopentathienyl, thienothienyl, oxadiazolopyrazinyl, benzofurazanyl, thiadiazolopyridinyl, triazolothiazinyl, triazolopyrimidinyl, triazolopyridinyl, benzotriazolyl, oxazolopyrimidinyl, oxazolopyridinyl, benzooxazolyl, thiazolopyridazinyl, thiazolopyrimidinyl, benzoisothiazolyl, benzothiazolyl, pyrazolotriazinyl, pyrazolothiazinyl, imidazopyrazinyl, purinyl, pyrazolopyridazinyl, pyrazolopyriminidyl, imidazopyridinyl, pyranopyrazolyl, benzoimidazolyl, indazolyl, benzooxathiolyl, benzodioxalyl, dithiolopyrimidinyl, benzodithiolyl, indolydinyl, indolyl, isoindolyl, furopyrimidinyl, furopyridinyl, benzofuranyl, isobenzofuranyl, thienopyrazinyl, thienopyrimidinyl, thienodioxynyl, thienopyridinyl, benzothienyl, isobenzothienyl, cyclopentaoxazinyl, cyclopentafuranyl, benzothiaziadinyl, benzotriazinyl, pyridooxadinyl, benzooxadinyl, pyrimidothiazinyl, benzothiazinyl, pyrimidopyridazinyl, pyrimidopyrimidinyl, pyridopyridazinyl, pyridopyrimidinyl, cinnolinyl, quinazolinyl, quinoxalinyl, benzoxathiinyl, benzodioxynyl, benzodithiinyl, naphthylidinyl, isoquinolinyl, quinolinyl, benzopyranyl, benzothiopyranyl, chromanyl, isochromanyl, indolinyl and the like, with preference given to benzooxazolyl, benzoimidazolyl and benzothienyl, and particular preference given to benzothienyl.

The "lower" means that the number of carbon atoms constituting the group is 1 to 6, preferably 1 to 4.

The lower alkyl is an alkyl having 1 to 6 carbon atoms, which is specifically methyl, ethyl, propyl, isopropyl, butyl, isobutyl, sec-butyl, tert-butyl, pentyl, isopentyl, neopentyl, tert-pentyl, hexyl, isohexyl, neohexyl and the like. Preferred are alkyl having 1 to 4 carbon atoms, which is specifically methyl, ethyl, propyl, isopropyl, butyl, isobutyl, sec-butyl and tert-butyl, with more preference given to methyl, ethyl and isopropyl, and particular preference given to methyl and ethyl.

The acyl is specifically exemplified by formyl, acetyl, propionyl, butyryl, isobutyryl, valeryl, benzoyl, naphthoyl, trioyl, saliciloyl and the like, with preference given to acyl having 1 to 4 carbon atoms, which is exemplified by formyl, acetyl, propionyl and butyryl.

The lower alkoxy is alkoxy having 1 to 6 carbon atoms, which is specifically methoxy, ethoxy, propoxy, butoxy, tert-butoxy, pentyloxy, hexyloxy and the like, with preference given to alkoxy having 1 to 4 carbon atoms, such as methoxy, ethoxy, propoxy, butoxy and tert-butoxy. Preferred are methoxy, ethoxy and tert-butoxy and more preferred are methoxy and ethoxy.

The aryloxy is exemplified by phenoxy, naphthyloxy, biphenyloxy and the like.

The aralkyloxy is exemplified by benzyloxy and the like.

The alkoxycarbonyl is exemplified by methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and the like. Preferred are alkoxycarbonyl having 2 to 5 carbon atoms, such as methoxycarbonyl, ethoxycarbonyl, propoxycarbonyl, butoxycarbonyl and tert-butoxycarbonyl. Preferred are methoxycarbonyl, ethoxycarbonyl and tert-butoxycarbonyl and particularly preferred are methoxycarbonyl and ethoxycarbonyl.

The aryloxycarbonyl is exemplified by phenoxycarbonyl, naphthyloxycarbonyl, biphenyloxycarbonyl and the like.

The aralkyloxycarbonyl is exemplified by benzyloxycarbonyl and the like.

The "optionally substituted" means optional substitution with 1 to 3 substituents wherein said substituents may be the same or different. Examples of the substituent include lower alkyl such as methyl, ethyl, propyl, butyl and tert-butyl; lower alkoxy such as methoxy, ethoxy, propoxy, butoxy, tert-butoxy, pentyloxy and hexyloxy; halogen atom such as fluorine atom, chlorine atom, bromine atom and iodine atom; nitro; cyano; hydroxy; acyl such as formyl, acetyl, propionyl, butyryl, isobutyryl, valeryl, benzoyl, naphthoyl, trioyl and saliciloyl; acyloxy such as formyloxy, acetyloxy, propionyloxy, butyryloxy, isobutyryloxy and benzoyloxy; aralkyloxy such as benzyloxy, phenethyloxy and phenylpropyloxy; mercapto; alkylthio such as methylthio, ethylthio, propylthio, butylthio, isobutylthio and tert-butylthio; amino; alkylamino such as methylamino, ethylamino, propylamino, isopropylamino and butylamino; dialkylamino such as dimethylamino, diethylamino, dipropylamino, diisopropylamino and dibutylamino; carbamoyl; alkoxycarbonyl such as methoxycarbonyl, ethoxycarbonyl, propoxycarbonyl, isopropoxycarbonyl, butoxycarbonyl, tert-butoxycarbonyl, pentyloxycarbonyl and hexyloxycarbonyl; alkylthiocarbonyl such as methylthiocarbonyl; amide; trifluoromethyl; phospholyl; sulfonyl; sulfonyloxy; sulfamoyl; alkylphosphonamide such as methylphosphonamide, ethylphosphonamide, propylphosphonamide and isopropylphosphonamide; methylenedioxy; alkoxyphospholyl such as methoxyphospholyl, ethoxyphospholyl, propoxyphospholyl and isopropoxyphospholyl; alkylsulfonyl such as methylsulfonyl, ethylsulfonyl, propylsulfonyl, butylsulfonyl and tert-butylsulfonyl; alkylsulfonylamino such as methylsulfonylamino, ethylsulfonylamino, propylsulfonylamino, butylsulfonylamino and tert-butylsulfonylamino; and the like.

The optionally substituted substituent at $R_7$ is preferably lower alkyl, acyl, carbamoyl and alkoxycarbonyl, and the optionally substituted substituent at $R_7'$ is preferably lower alkyl, acyl, carbamoyl and alkoxycarbonyl. The optionally substituted substituent at $R_9$ is preferably alkoxycarbonyl, and the optionally substituted substituent at $R_{10}$ is preferably lower alkyl, acyl, carbamoyl, alkoxycarbonyl and alkylthiocarbonyl.

The pharmaceutically acceptable salt may be any as long as it forms nontoxic salt with the novel propionic acid derivative of the above formula (I). Examples thereof include alkali metal salts such as sodium salt and potassium salt; alkaline earth metal salts such as magnesium salt and calcium salt; ammonium salt; organic base salts such as trimethylamine salt, triethylamine salt, pyridine salt, picoline salt, dicyclohexylamine salt and N,N'-dibenzylethylenediamine salt; amino acid salts such as lysine salt and arginine salt; and the like.

The derivative (hereinafter to be referred to as derivative (I')) of the formula (I')

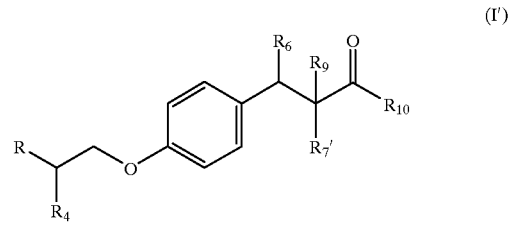

(I')

wherein
R is a group of the formula

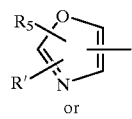

or

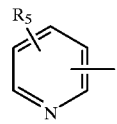

wherein R' is an optionally substituted aromatic hydrocarbon, an optionally substituted alicyclic hydrocarbon, an optionally substituted heterocyclic group or an optionally substituted fused heterocyclic group, and $R_5$ is a lower alkyl;

$R_4$, is a hydrogen atom or a lower alkyl;

$R_6$ is a hydrogen atom or forms, together with $R_9$, a double bond;

$R_7'$ is a hydrogen atom, a hydroxy, a carboxy, an acyl, an optionally substituted alkoxycarbonyl, an optionally substituted lower alkyl, an optionally substituted carbamoyl, an optionally substituted aryloxycarbonyl, an optionally substituted aralkyloxycarbonyl or a group of the formula —Y—$R_8$ wherein Y is NH or oxygen atom and $R_8$ is optionally substituted-acyl, optionally substituted alkoxycarbonyl, aryloxycarbonyl or aralkyloxycarbonyl;

$R_9$ is a hydrogen atom, an optionally substituted lower alkyl or an optionally substituted lower alkoxycarbonyl; and $R_{10}$ is a hydroxy, an optionally substituted amino, an optionally substituted lower alkoxy, an optionally substituted lower alkyl, an optionally substituted aryloxy or an optionally substituted aralkyloxy has superior hypoglycemic action and hypolipidemic action and is useful for the prophylaxis and treatment of diabetes mellitus and hyperlipemia, and for the prophylaxis of arteriosclerosis. When the derivative (I') and pharmaceutically acceptable salts thereof are used as pharmaceutical preparations, they are generally admixed with pharmacologically acceptable carrier, excipients, diluents, extenders, disintegrators, stabilizers, preservatives, buffering agents, emulsifiers, aromatics, colorings, sweeteners, thickners, flavors, solubilizers and other additives such as water, vegetable oil, alcohols such as ethanol and benzyl alcohol, polyethylene glycol, glycerol triacetate, gelatin, lactose, carbohydrate such as starch, magnesium stearate, talc, lanoline, petrolatum and the like and prepared into tablets, pills, powders, granules, suppositories, injections, eye drops, liquids, capsules, troches, aerosols, elixils, suspensions, emulsions, syrups and the like, and administered orally or parenterally. The dose varies depending on the kind and degree of diseases, compound to be administered and administration route, age, sex and body weight of patients, and the like. In the case of oral administration, the daily dose of the derivative (I') is generally 0.01–1000 mg, particularly 0.05–100 mg, for an adult.

The derivative (hereinafter to be referred to as derivative (I)) of the above-mentioned formula (I)

(I)

wherein R, $R_4$, $R_6$, $R_7$, $R_9$ and $R_{10}$ are as defined above, provided that when $R_7$ is alkoxycarbonyl and $R_9$ is hydrogen atom, $R_{10}$ is not lower alkoxy, includes hydrates thereof, solvates thereof (e.g., ethanol and organic solvent which is acceptable as a pharmaceutical product), prodrug thereof (e.g., pivaloylmethyl ester and 1-(ethoxycarbonyloxy)ethyl ester) and active metabolites thereof, all of which are encompassed in the scope of the present invention. The derivative (I) has one or more asymmetric carbon. When it has one asymmetric carbon, a pure optically active compound, a mixture thereof in an optional proportion, or a racemate exists; and when it has two or more asymmetric carbons, optically pure diastereomer, lacemate thereof, a combination thereof and a mixture in an optional proportion exist, all of which fall within the scope of the present invention. Hydrates are also encompassed. As is evident from the structure, the derivative (I) can occur as a keto-enol tautomer which also falls within the scope of the present invention.

The derivative (I) can be synthesized by the following method. It is needless to say that the production method of the compounds of the present invention is not limited to those exemplified below.

Producton Method A

When a compound wherein $R_7$ is carboxy, optionally substituted alkoxycarbonyl or optionally substituted carbamoyl is desired, the compound can be produced by the following method.

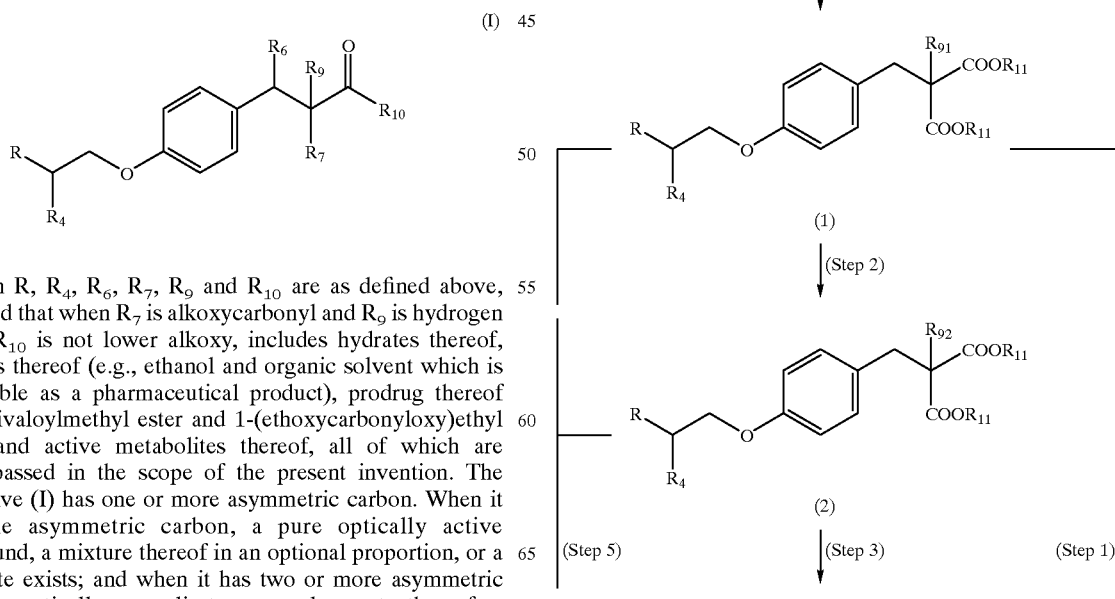

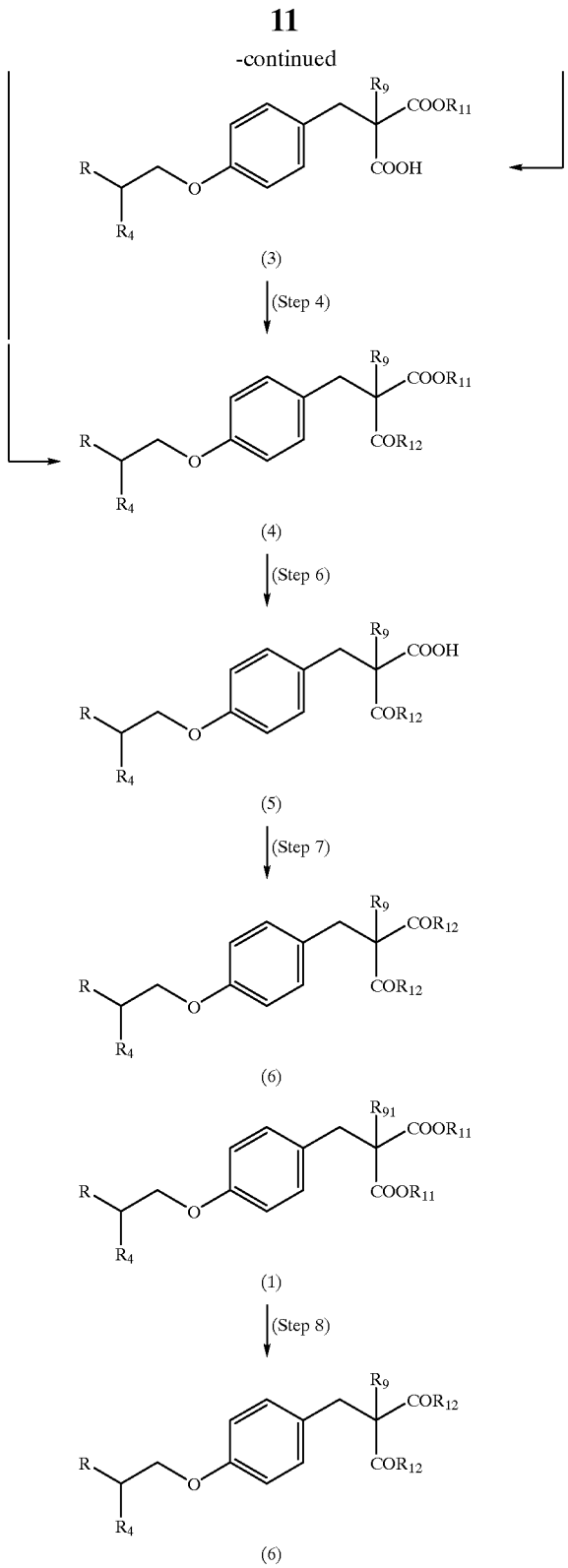

wherein $R_{11}$ is lower alkyl, benzyl or phenyl, $R_{11}'$ is lower alkyl, benzyl, phenyl, lower alkoxy, benzyloxy, phenoxy or optionally substituted amino, $R_{12}$ is optionally substituted amino, lower alkyl, benzyl or phenyl, $R_{91}$ is hydrogen atom, $R_{92}$ is lower alkyl and R, $R_4$, and $R_9$ are as defined above.

(Step a)

Compound (c) can be synthesized by refluxing under heating the compounds (a) and (b) synthesized according to the method described in Japanese Patent Unexamined Publication No. 139182/1988 or WO95/18125, using a catalyst such as piperidinium acetate prepared from acetic acid and piperidine in this sytem, ethylenediammonium diacetate and ammonium acetate in an organic solvent such as toluene and benzene while removing water from the system.

While the reaction conditions such as temperature and time vary depending on the kind of starting compound and solvent, the reaction generally proceeds from room temperature to under heating, preferably under heating, for several dozen minutes to several hours.

(Step b)

Compound (1) can be synthesized by reacting compound (c) in an organic solvent such as methanol, ethanol, propanol, isopropanol, tetrahydrofuran, dioxane, dichloromethane and acetic acid, or a mixed solvent thereof, using a catalyst such as palladium carbon and palladium black under a hydrogen atmosphere at room temperature to under heating for several hours.

(Step 1)

Compound (3) can be synthesized by dissolving compound (1) in an organic solvent such as alcohols (e.g., methanol, ethanol, propanol, isopropanol, butanol and ethylene glycol); ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); ketones (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; carbon disulfide; pyridine; and hexamethyl phosphotriamide, or an inorganic solvent (e.g., water), or a mixture thereof and adding an equivalent of a base such as sodium hydroxide, potassium hydroxide, lithium hydroxide, barium hydroxide, sodium carbonate and potassium carbonate.

While the reaction conditions such as temperature and time vary depending on the kind of starting compound and solvent, the reaction generally proceeds from ice-cooling to under heating, preferably ice-cooling to room temperature, for several minutes to several dozen hours.

(Step 2)

Compound (2) can be synthesized by dissolving compound (1) in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); ketones (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; carbon disulfide; pyridine; and hexamethyl phosphotriamide, or an inorganic solvent (e.g., water and hydrochloric acid), adding a deprotonizing agent such as lithium diisopropylamine, sodium hydride, and potassium carbonate, and then reacting the resulting mixture with halogenated alkyl such as methyl iodide and ethyl iodide, or halogenated acetate such as ethyl bromoacetate.

While the reaction conditions such as temperature and time vary depending on the kind of starting compound and solvent, the reaction generally proceeds from −80° C. to under heating, preferably −80° C. to room temperature, for several minutes to several dozen hours.

(Step 3)
Compound (3) can be synthesized by subjecting compound (2) to a method similar to Production A, Step 1).
(Step 4)
Compound (4) can be synthesized by dissolving compound (3) in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters such as methyl acetate and ethyl acetate; ketones (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; carbon disulfide; piperidine; and hexamethyl phosphotriamide, or without solvent, adding halogenating agent such as thionyl chloride, oxalyl chloride, phophorus trichloride and phophorus pentachloride, and, where necessary, adding an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters (e.g., methyl acetate and ethyl acetate); ketones (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; carbon disulfide; piperidine; and hexamethylphosphoric triamide, and reacting the resulting mixture with aqueous ammonia, methyl carbamate, urea, alkylamine (e.g., aqueous methylamine and dimethylamine), acetamide, alcohols such as methanol, ethanol and isopropanol or other nucleating agent.

While the reaction conditions such as temperature and time vary depending on the kind of starting compound and solvent, the reaction generally proceeds from −78° C. to under heating, preferably room temperature to under heating, for several minutes to several dozen hours.

Alternatively, compound (3) is dissolved in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters such as methyl acetate and ethyl acetate; hydrocarbons (e.g., n-hexane and cyclohexane); aprotic polar solvents (e.g., N,N-dimethylformamide); acetonitrile; dimethyl sulfoxide; carbon disulfide; piperidine; and hexamethylphosphoric triamide, and a base (e.g., sodium hydrogencarbonate) and then halogenated alkyl such as methyl iodide and ethyl iodide, or halogenated benzyl such as benzyl iodide or halogenated phenyl such as phenyl iodide are added.

While the reaction conditions such as temperature and time vary depending on the kind of starting compound and solvent, the reaction generally proceeds from −78° C. to under heating, preferably room temperature to under heating, for several minutes to several dozen hours.

Alternatively, compound (3) is reacted with a nucleophilic agent such as a base (e.g., 4-dimethylaminopyridine) and alcohols (e.g., phenol, methanol and ethanol) in ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters such as methyl acetate and ethyl acetate; hydrocarbons (e.g., n-hexane and cyclohexane); aprotic polar solvents (e.g., N,N-dimethylformamide); methylene chloride; acetonitrile; dimethyl sulfoxide; carbon disulfide; pyridine; or hexamethylphosphoric triamide, using N,N'-dicyclohexylcarbodiimide or water soluble carbodiimide hydrochloride as a condensing agent, and adding, as necessary, dehydrating agent such as molecular sieves 4A powder.

A similar reaction can be carried out by using a reactive derivative of carboxylic acid, such as corresponding active ester (e.g., N-hydroxysuccinimide ester and N-hydroxybenzotriazol ester), acid azide or a mixed acid anhydride.

While the reaction conditions such as temperature and time vary depending on the kind of starting compound and solvent, the reaction generally proceeds from −78° C. to under heating, preferably room temperature to under heating, for several minutes to several dozen hours.
(Step 5)
Compound (4) can be synthesized by dissolving compound (1) or (2) in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters (e.g., methyl acetate and ethyl acetate); ketones (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; carbon disulfide; pyridine; and hexamethylphosphoric triamide, or water, or without solvent, and reacting the resulting mixture with aqueous ammonia, amine such as alkylamine (e.g., aqueous methylamine and dimethylamine) or other nucleophilic agent.

While the reaction conditions such as temperature and time vary depending on the kind of starting compound and solvent, the reaction generally proceeds from 0° C. to under heating, preferably room temperature to under heating, for several minutes to several dozen hours.
(Step 6)
Compound (5) can be synthesized by subjecting compound (4) to a method similar to Production A, Step 1).

Alternatively, compound (4) is dissolved in an organic solvent such as alcohols (e.g., methanol, ethanol, propanol, isopropanol, butanol and ethylene glycol); ethers (e.g., diethyl ether, tetrahydrofuran, diglyme, 1,4-dioxane and 1,2-dimethoxyethane); aromatic hydrocarbons (e.g., benzene, toluene and xylene); halogenated hydrocarbons (e.g., chloroform, dichloromethane, 1,2-dichloroethane, carbon tetrachloride and tetrachloroethane); esters such as methyl acetate and ethyl acetate; ketones (e.g., acetone and methyl ethyl-ketone); hydrocarbons (e.g., n-hexane and cyclohexane); aprotic polar solvents (e.g., N,N-dimethylformamide); acetonitrile; dimethyl sulfoxide; sulfolane; carbon disulfide; pyridine; hexamethylphosphoric triamide; formic acid; and acetic acid, or inorganic solvent such as water, or a mixed solvent thereof, and reacted under a hydrogen atmosphere in the presence of a catalyst such as palladium carbon, platinum oxide and Raney nickel.

While the reaction conditions such as temperature and time vary depending on the kind of starting compound and solvent, the reaction generally proceeds from ice-cooling to under heating, preferably room temperature to under heating, for several minutes to several hours.

(Step 7)
Compound (6) can be synthesized by subjecting compound (5) to a method similar to Production A, Step 4).
(Step 8)
Compound (6) can be synthesized by subjecting compound (1) to a method similar to Production A, Step 5).

Producton Method B

When a compound wherein $R_7$ is hydrogen atom is desired, the compound can be produced by the following method.

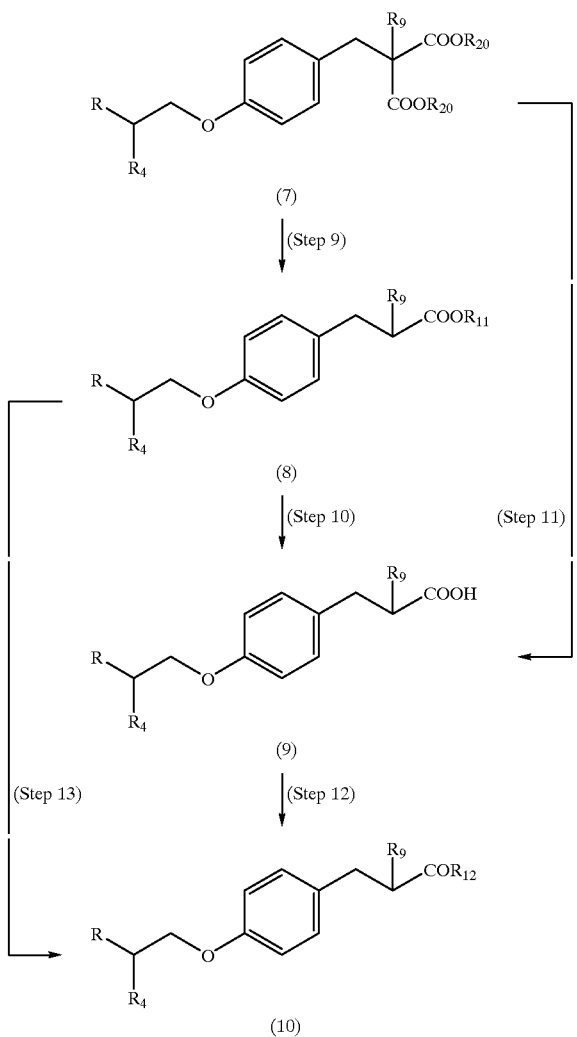

wherein $R_{20}$ may be the same or different and each is hydrogen atom, lower alkyl or benzyl and R, $R_4$, $R_9$, $R_{11}$ and $R_{12}$ are as defined above.
(Step 9)
Compound (8) can be synthesized by dissolving compound (7) synthesized according to the method described in WO95/18125 in an organic solvent such as an aprotic polar solvent (e.g., N,N-dimethyl sulfoxide) and hexamethyl phosphotriamide, or inorganic solvent (e.g., water), or without solvent, adding halogenated alkyl metal such as lithium chloride, sodium chloride and sodium iodide, alkali metal cyanate such as sodium cyanate and potassium cyanate or inorganic salt of acetic acid, such as sodium acetate, potassium acetate, methyl ammoniumtetraacetate ($Me_4NOAc$), and refluxing the mixture under heating.

While the reaction conditions such as temperature and time vary depending on the kind of starting compound and solvent, the reaction generally proceeds from room temperature to under heating, preferably room temperature to 250° C., for several minutes to several hours.
(Step 10)
Compound (9) can be synthesized by dissolving compound (8) in an organic solvent such as alcohols (e.g., methanol, ethanol, propanol, isopropanol, butanol and ethylene glycol); ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); ketons (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; carbon disulfide; pyridine; hexamethylphosphoric triamide; or inorganic solvent such as water, or a mixture thereof, and treating the resulting solution with a base such as sodium hydroxide, lithium hydroxide, barium carbonate, sodium carbonate and potassium carbonate.

While the reaction conditions such as temperature and time vary depending on the kind of starting compound and solvent, the reaction generally proceeds from 0° C. to under heating, preferably room temperature to under heating, for several minutes to several dozen hours.
(Step 11)
Compound (9) can be synthesized from compound (7) dissolved in an organic solvent such as ethers (e.g., tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters such as methyl acetate and ethyl acetate; hydrocarbons (e.g., n-hexane and cyclohexane); aprotic polar solvents (e.g., N,N-dimethylformamide); acetonitrile; dimethyl sulfoxide; carbon disulfide; pyridine; hexamethylphosphoric triamide; p-toluenesulfonic acid; benzenesulfonic acid; methanesulfonic acid; trifluoromethanesulfonic acid; formic acid; and acetic acid or inorganic solvent such as water, hydrochloric acid, sulfric acid and hydrobromic acid, or without dissolving same in a solvent.

While the reaction conditions such as temperature and time vary depending on the kind of starting compound and solvent, the reaction generally proceeds from room temperature to under heating and under heating when solvent is not used, for several minutes to several hours.
(Step 12)
Compound (10) can be synthesized by subjecting compound (9) to a method similar to Production A, Step 4).

Compound (10) can be also synthesized by dissolving compound (9) in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride; and hydrocarbons (e.g., n-hexane and cyclohexane); or without solvent, and reacting same with alkyl cyanate such as methyl isocycnate or alkyl thiocyanate such as methyl thiocyanate in the presence of Lewis acid such as tin tetrachloride and titanium tetrachloride, carboxylic acid such as formic acid and acetic acid or an acid such as hydrochloric acid.

While the reaction conditions such as temperature and time vary depending on the kind of starting compound and solvent, the reaction generally proceeds from ice-cooling to under heating, preferably room temperature to under heating, for several minutes to several dozen hours.

(Step 13)

Compound (10) can be synthesized by subjecting compound (8) to a method similar to Production A, Step 5).

Production Method C

When a compound wherein $R_7$ is a group of the formula —Y—$R_8$ wherein Y and $R_8$ are as defined above, is desired, the compound can be produced by the following method.

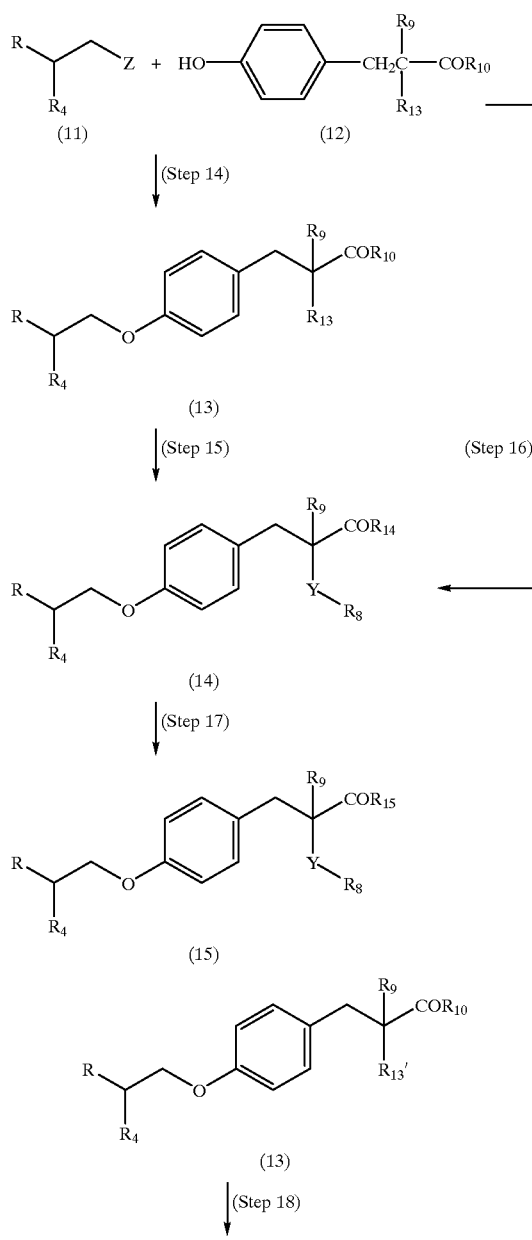

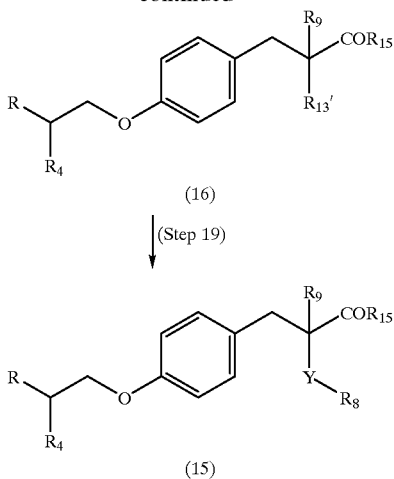

wherein Z is a leaving group such as p-toluenesulfonyloxy, benzenesulfonyloxy, methanesulfonyloxy and halogen atom, and $R_{13}$ is hydrogen atom, hydroxy, amino or a group of the formula —Y—$R_8$ wherein Y and $R_8$ are as defined above, $R_{13}'$ is hydrogen atom, hydroxy or amino, $R_{14}$ is optionally substituted lower alkoxy and $R_{15}$ is optionally substituted amino, and R, $R_4$, $R_9$ and $R_{10}$ are as defined above.

(Step 14)

Compound (13) can be synthesized by dissolving compound (12) wherein $R_{13}$ is hydrogen atom, hydroxy or amino, and other symbols are as defined above, in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); hydrocarbons (e.g., n-hexane and cyclohexane); aprotic polar solvents (e.g., N,N-dimethylformamide); acetonitrile; dimethyl sulfoxide; sulfolane; carbon disulfide; pyridine; and hexamethylphosphoric triamide, and reacting same with compound (11) synthesized according to the method described in WO95/18125, in the presence of a base such as alkali metal or alkaline earth metal hydride (e.g., sodium hydride and potassium hydride); alkali metal alkolate (e.g., sodium methoxide and potassium tert-butoxide); and lithium alkylamide (e.g., lithium diisopropylamide).

While reaction conditions such as temperature and time vary depending on the kind of starting compound and solvent, the reaction generally proceeds at −80° C. to under heating, for several minutes to several hours.

(Step 15)

Compound (14) can be synthesized by dissolving compound (13) in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters (e.g., methyl acetate and ethyl acetate); ketones (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; sulfolane; carbon disulfide; pyridine; and hexamethylphosphoric triamide, or inorganic solvent such as water, and reacting same with acid halide such as acetyl chloride, halogenated carbonate such as methyl chlorocarbonate, or acid anhydride such as acetic anhydride, in the presence of an organic base such as pyridine and triethylamine or an inorganic base such as sodium hydroxide and sodium carbonate.

While reaction conditions such as temperature and time vary depending on the kind of starting compound and solvent, the reaction generally proceeds at −80° C. to under heating, preferably −80° C. to room temperature, for several minutes to several dozen hours.

(Step 16)

Compound (14) can be synthesized by subjecting compound (12) wherein $R_{13}$ is a group of the formula —Y—$R_8$ wherein Y and $R_8$ are as defined above, and other symbols are as defined above, to a method similar to Production C, Step 14).

(Step 17)

Compound (15) can be synthesized by subjecting compound (14) to a method similar to Production A, Step 5).

(Step 18)

Compound (16) can be synthesized by subjecting compound (13) to a method similar to Production A, Step 5).

(Step 19)

Compound (15) can be synthesized by subjecting compound (16) to a method similar to Production B, Step 15).

Production Method D

A compound wherein $R_7$ is carboxy and $R_{10}$ is hydroxy can be produced by the following steps.

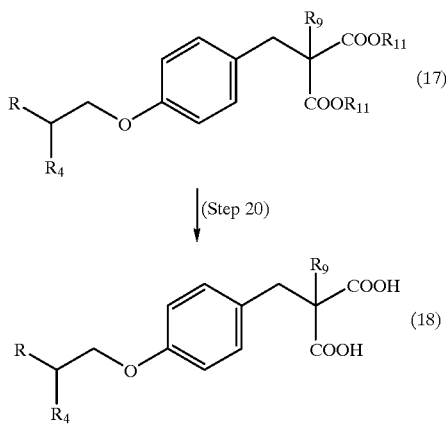

wherein R, $R_4$, $R_9$ and $R_{11}$ are as defined above.
(Step 20)

Compound (18) can be synthesized by dissolving compound (17) synthesized according to the method described in WO95/18125 in an organic solvent such as alcohols (e.g., methanol, ethanol, propanol, isopropanol, butanol and ethylene glycol); ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); ketones (e.g., acetone and methyl ethyl ketone); hydrocarbons (e.g., n-hexane and cyclohexane); aprotic polar solvents (e.g., N,N-dimethylformamide); acetonitrile; dimethyl sulfoxide; carbon disulfide; pyridine; and hexamethylphosphoric triamide, or an inorganic solvent such as water, or a mixed solvent thereof, and treating same with a base such as sodium hydroxide, potassium hydroxide, lithium hydroxide, barium hydroxide, sodium carbonate and potassium carbonate.

While reaction conditions such as temperature and time vary depending on the kind of starting compound and solvent, the reaction generally proceeds at 0° C. to under heating, preferably room temperature to under heating, for several minutes to several dozen hours.

Compound (18) wherein $R_{11}$ is benzyl and other symbols are as defined above can be synthesized by dissolving compound (17) synthesized according to the method described in WO95/18125 in an organic solvent such as alcohols (e.g., methanol, ethanol, propanol, isopropanol, butanol and ethylene glycol); ethers (e.g., diethyl ether, tetrahydrofuran, diglyme, 1,4-dioxane and 1,2-dimethoxyethane); aromatic hydrocarbons (e.g., benzene, toluene and xylene); halogenated hydrocarbons (e.g., chloroform, dichloromethane, 1,2-dichloroethane, carbon tetrachloride and tetrachloroethane); esters (e.g., methyl acetate and ethyl acetate); ketones (e.g., acetone and methyl ethyl ketone); hydrocarbons (e.g., n-hexane and cyclohexane); aprotic polar solvents (e.g., N,N-dimethylformamide); acetonitrile; formic acid; and acetic acid, or an inorganic solvent such as water or a mixed solvent thereof, and reacting same using a catalyst such as palladium carbon, platinum oxide and Raney nickel under a hydrogen atmosphere at room temperature.

While reaction conditions such as temperature and time vary depending on the kind of starting compound and solvent, the reaction generally proceeds at ice-cooling to under heating, preferably room temperature to under heating, for several minutes to several hours.

Production Method E

A compound wherein $R_7$ is carboxy and $R_{10}$ is amino can be produced by the following steps.

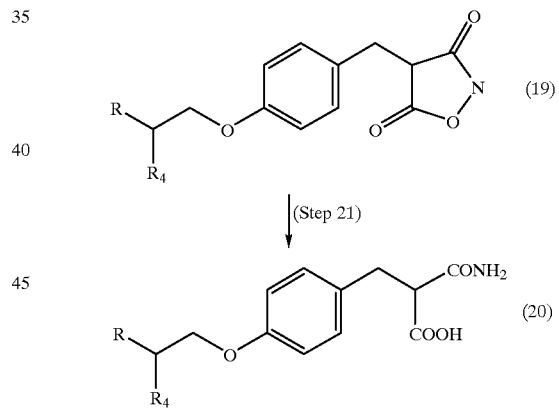

wherein R, and $R_4$ and $R_6$ are as defined above.
(Step 21)

Compound (20) can be synthesized by dissolving compound (19) synthesized according to the method described in WO95/18125 in an organic solvent such as alcohols (e.g., methanol, ethanol, propanol, isopropanol, butanol and ethylene glycol); ethers (e.g., diethyl ether, tetrahydrofuran, diglyme, 1,4-dioxane and 1,2-dimethoxyethane); aromatic hydrocarbons (e.g., benzene, toluene and xylene); halogenated hydrocarbons (e.g., chloroform, dichloromethane, 1,2-dichloroethane, carbon tetrachloride and tetrachloroethane); esters (e.g., methyl acetate and ethyl acetate); ketones (e.g., acetone and methyl ethyl ketone); hydrocarbons (e.g., n-hexane and cyclohexane); aprotic polar solvents (e.g., N,N-dimethylformamide); acetonitrile; formic acid; and acetic acid, or an inorganic solvent such as water or a mixed solvent thereof, and reacting same using a catalyst such as palladium carbon, platinum oxide and Raney nickel under a hydrogen atmosphere at room temperature.

While reaction conditions such as temperature and time vary depending on the kind of starting compound and solvent, the reaction generally proceeds at ice-cooling to under heating, preferably room temperature to under heating, for several minutes to several hours.

Production Method F

A compound wherein $R_7$ is carboxy can be produced by the following steps.

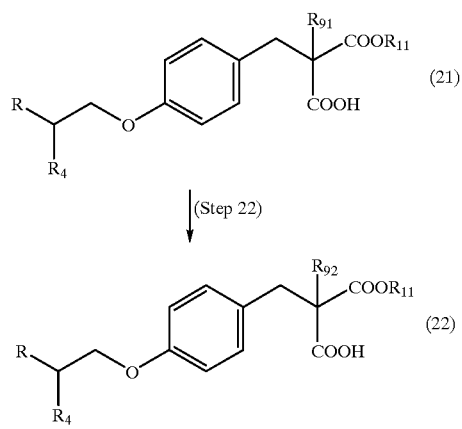

wherein R, $R_4$, $R_{11}$, $R_{91}$ and $R_{92}$ are as defined above.

(Step 22)

Compound (22) can be synthesized by subjecting compound (21) synthesized according to Production A, Step 1) to a method similar to Production A, Step 2).

Production Method G

A compound wherein $R_7$ is optionally substituted alkoxycarbonyl, aryloxycarboxy or aralkyloxycarbonyl can be produced by the following steps.

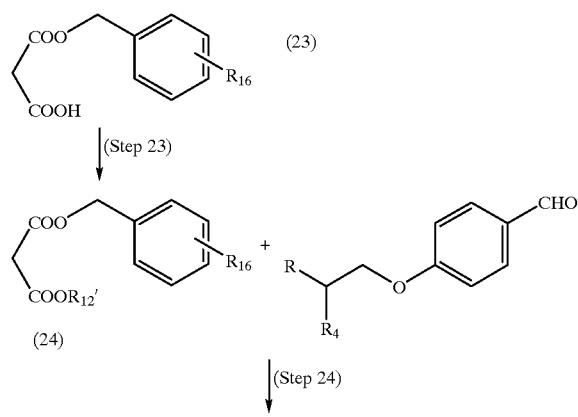

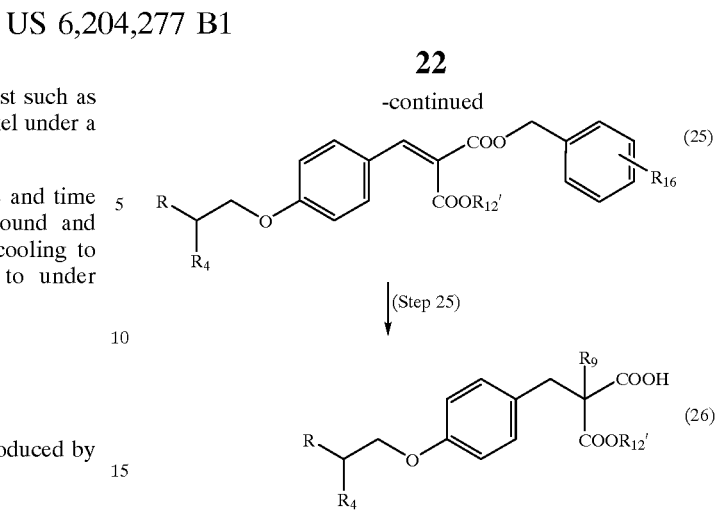

wherein $R_{16}$ is halogen atom such as chlorine atom, bromine atom and iodine atom, carboxy, amino, lower alkyl, nitro, lower alkoxy, alkoxycarbonyl, acyl, benzyl or phenyl, $R_{12}'$ is lower alkyl, benzyl or phenyl, R, $R_4$, and $R_9$ are as defined above.

(Step 23)

Compound (24) can be synthesized by subjecting compound (23) to a method similar to Production A, Step 4).

(Step 24)

Compound (25) can be synthesized by subjecting compound (24) and compound a) to a method similar to Production A, Step a).

(Step 25)

Compound (26) can be synthesized by dissolving compound (25) in an organic solvent such as alcohols (e.g., methanol, ethanol, propanol, isopropanol, butanol and ethylene glycol); ethers (e.g., diethyl ether, tetrahydrofuran, diglyme, 1,4-dioxane and 1,2-dimethoxyethane); aromatic hydrocarbons (e.g., benzene, toluene and xylene); halogenated hydrocarbons (e.g., chloroform, dichloromethane, 1,2-dichloroethane, carbon tetrachloride and tetrachloroethane); esters (e.g., methyl acetate and ethyl acetate); ketones (e.g., acetone and methyl ethyl ketone); hydrocarbons (e.g., n-hexane and cyclohexane); aprotic polar solvents (e.g., N,N-dimethylformamide); acetonitrile; and organic acid (e.g., formic acid and acetic acid), or an inorganic solvent such as water or a mixed solvent thereof, and reacting same using a catalyst such as palladium carbon, platinum oxide and Raney nickel under a hydrogen atmosphere at room temperature.

While reaction conditions such as temperature and time vary depending on the kind of starting compound and solvent, the reaction generally proceeds at ice-cooling to under heating, preferably room temperature to under heating, for several minutes to several hours.

Production Method H

A compound wherein $R_7$ is optionally substituted aralkyloxycarbonyl can be produced by the following steps.

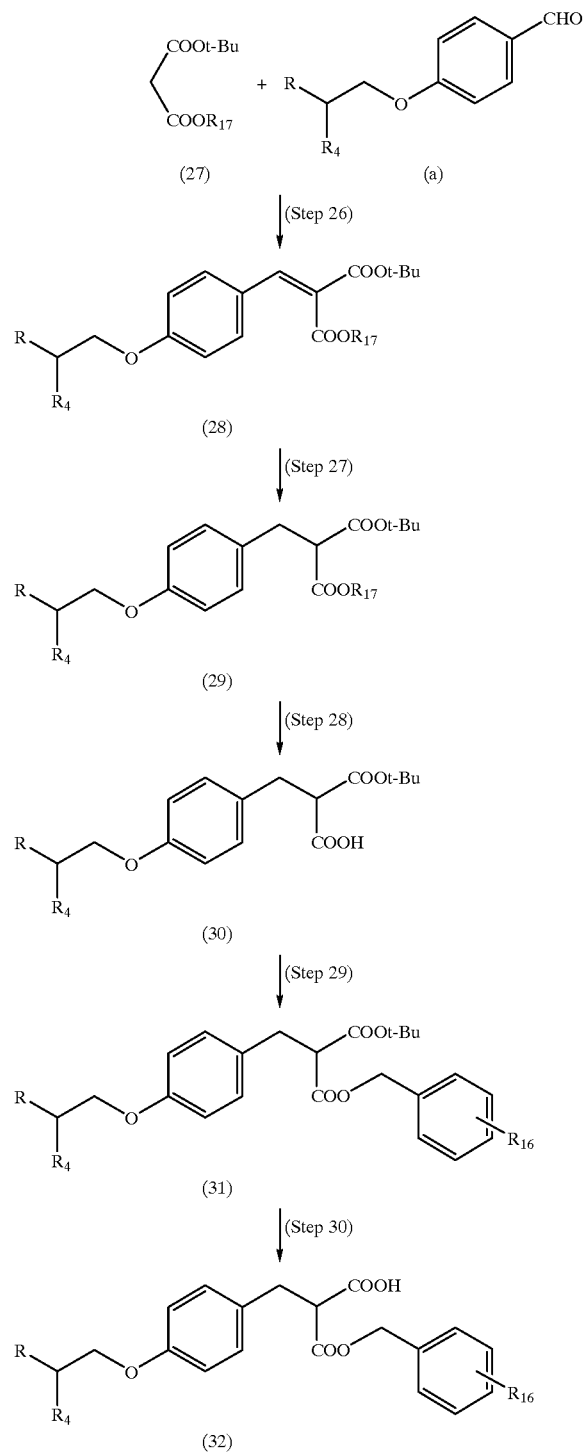

wherein $R_{17}$ is lower alkyl and R, $R_4$, and $R_{16}$ are as defined above.

(Step 26)

Compound (28) can be synthesized by subjecting compound (27) and compound a) to a method similar to Production A, Step a).

(Step 27)

Compound (29) can be synthesized by subjecting compound (28) to a method similar to Production G, Step 25).

(Step 28)

Compound (30) can be synthesized by subjecting compound (29) to a method similar to Production A, Step 1).

(Step 29)

Compound (31) can be synthesized by subjecting compound (30) to a method similar to Production A, Step 4).

(Step 30)

Compound (32) can be synthesized by dissolving compound (31) in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); hydrocarbons (e.g., n-hexane and cyclohexane); aprotic polar solvents (e.g., N,N-dimethylformamide); methylene chloride; and acetonitrile, or an inorganic solvent such as water, hydrochloric acid, sulfuric acid and hydrobromic acid or a mixed solvent thereof, and adding an acid such as formic acid, trifluoroacetic acid and p-toluene sulfonic acid, or reacting same in p-toluenesulfonic acid, benzenesulfonic acid, methanesulfonic acid, trifluoromethanesulfonic acid, formic acid or acetic acid.

While reaction conditions such as temperature and time vary depending on the kind of starting compound and solvent, the reaction generally proceeds at 0° C. to under heating for several minutes to several hours.

Production Method I

A compound wherein $R_7$ is carboxy and $R_{10}$ is lower alkoxy can be produced by the following steps.

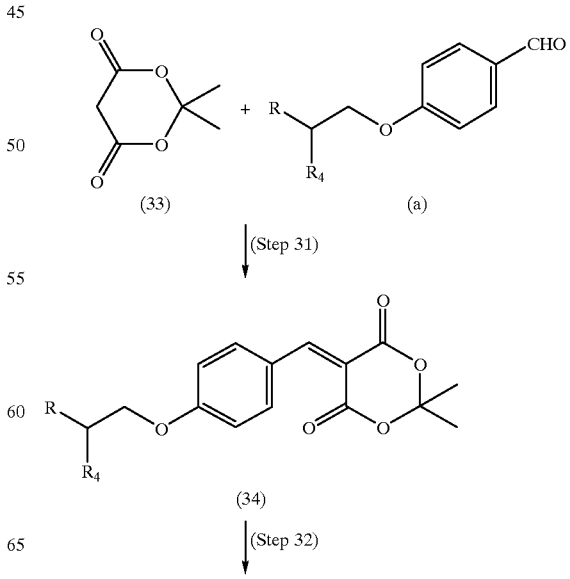

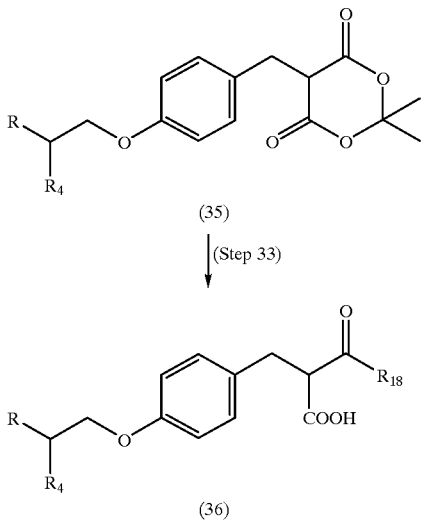

(35)

(Step 33)

(36)

wherein $R_{18}$ is optionally substituted lower alkoxy and R, and $R_4$, are as defined above.

(Step 31)

Compound (34) can be synthesized by subjecting compound (33) and compound (a) to a method similar to Production A, Step a).

(Step 32)

Compound (35) can be synthesized by subjecting compound (34) to a method similar to Production C, Step 25).

(Step 33)

Compound (36) can be synthesized by reacting compound (35) in an organic solvent such as ethers (e.g., diethyl ether, tetrahydrofuran, diglyme, 1,4-dioxane and 1,2-dimethoxyethane); aromatic hydrocarbons (e.g., benzene, toluene, nitrobenzene and xylene); halogenated hydrocarbons (e.g., chloroform, dichloromethane, 1,2-dichloroethane, carbon tetrachloride and tetrachloroethane); esters (e.g., methyl acetate and ethyl acetate); ketones (e.g., acetone and methyl ethyl ketone); hydrocarbons (e.g., n-hexane and cyclohexane); aprotic polar solvents (e.g., N,N-dimethylformamide); methylene chloride; acetonitrile; dimethyl sulfoxide; carbon disulfide; pyridine; and hexamethylphosphoric triamide, or an inorganic solvent such as water or a mixed solvent thereof, or without solvent, with a nucleophilic agent such as alcohols, amines and silylated compound thereof.

While reaction conditions such as temperature and time vary depending on the kind of starting compound and solvent, the reaction generally proceeds at 0° C. to under heating, for several minutes to several dozen hours.

The above-mentioned steps may include further steps of filtration, extraction, washing, concentration, drying, purification and the like.

The present invention is described in detail by way of Examples. In the Examples, "%" means "wt %" unless otherwise specified. It is needless to say that the present invention is not limited to the following Examples.

EXAMPLE 1

2-Methoxycarbonyl-3-[4-[2-(5-methyl-2-phenyl-4-oxazolyl)ethoxy]phenyl]propionic acid Dimethyl 2-[4-[2-(5-methyl-2-phenyl-4-oxazolyl)ethoxy] benzyl]malonate (8.46 g, 20 mmol) synthesized according to the method described in WO95/18125 was dissolved in a mixture of methanol (80 ml) and tetrahydrofuran (40 ml), and 2N aqueous sodium hydroxide solution (11 ml, 22 mmol) was added at 0° C. The mixture was stirred for 1.5 hr at room temperature and the solvent was evaporated. A saturated aqueous solution (5 ml) of sodium hydrogencarbonate was added and the aqueous layer was washed with ethyl acetate. To the obtained aqueous layer was added sodium chloride to saturate the solution, and the mixture was acidified with 1N hydrochloric acid and washed three times with ethyl acetate (50 ml). The extracted organic layers were combined, washed with brine, dried over sodium sulfate and dried to solidness to give a crude title compound (8.2 g, yield 100%). The obtained crude compound (750 mg) was recrystallized from a mixed solvent of ethyl acetate-hexane (1:2) to give the title compound (540 mg) as a white solid.

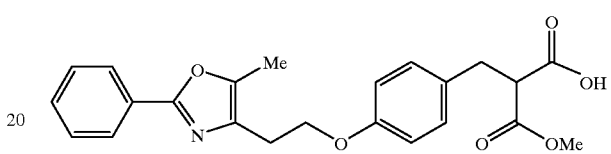

mp: 126.0–127.1° C.;
$^1$H-NMR(CDCl$_3$) δ ppm, 300 MHz: 2.36(3H, s), 2.96(2H, t, J=6.5 Hz), 3.19(2H, d, J=7.5 Hz), 3.65(1H, t, J=7.5 Hz), 3.71(3H, s), 4.15(2H, t, J=6.6 Hz), 6.79(2H, d, J=8.4 Hz), 7.11(2H, d, J=8.4 Hz), 7.42(3H, m), 7.95(2H, m).

EXAMPLE 2

Methyl 2-carbamoyl-3-[4-[2-(5-methyl-2-phenyl-4-oxazolyl)ethoxy]phenyl]propionate 2-Methoxycarbonyl-3-[4-[2-(5-methyl-2-phenyl-4-oxazolyl)ethoxy]phenyl]propionic acid (2.10 g, 5.10 mmol) obtained in Example 1 was dissolved in benzene (20 ml) and thionyl chloride (375 μl, 6.12 mmol) was dropwise added at room temperature. This mixture was refluxed under heating for 1.5 hr and the solvent was evaporated. The residue was dissolved in acetone (2 ml) and added to 28% aqueous ammonia (5 ml) at room temperature. The mixture was stirred for 30 min and the solvent was evaporated. Ethyl acetate (50 ml) was added to the residue and the organic layer was washed with brine, dried over sodium sulfate and dried to solidness to give a crude title compound (1.80 g, yield 86%). The obtained compound (1.50 g) was recrystallized from a mixed solvent of ethyl acetate-hexane (5:1) to give the title compound (700 mg, yield 40%) as a white powder.

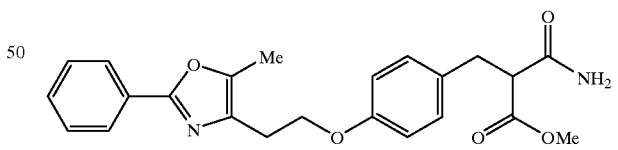

mp: 154.8–155.4° C.;
$^1$H-NMR(CDCl$_3$) δ ppm, 300 MHz: 2.36(3H, s), 2.96(2H, t, J=6.7 Hz), 3.17(2H, m), 3.47(1H, dd, J=6.7 and 8.2 Hz), 3.65(3H, s), 4.21(2H, t, J=6.7 Hz), 5.43(1H, brs), 6.38(1H, brs), 6.81(2H, d, J=8.6 Hz), 7.07(2H, d, J=8.6 Hz), 7.42(3H, m), 7.97(2H, m).

EXAMPLE 3

2-Carbamoyl-3-[4-[2-(5-methyl-2-phenyl-4-oxazolyl)ethoxy]phenyl]propionic acid

Methyl 2-carbamoyl-3-[4-[2-(5-methyl-2-phenyl-4-oxazolyl)ethoxy]phenyl]propionate (1.80 g, 4.41 mmol)

obtained in Example 2 was dissolved in methanol (20 ml) and tetrahydrofuran (20 ml), and 2.5N aqueous sodium hydroxide solution (2.5 ml, 6.16 mmol) was added at room temperature. The mixture was stirred for 15 hr and the solvent was evaporated. To the residue was added 10% aqueous sodium hydroxide solution (50 ml) and the mixture was washed three times with ethyl acetate (30 ml). To the aqueous layer was added sodium chloride to saturate the same, and the mixture was acidified with 3N hydrochloric acid. The precipitated white solid was collected by filtration, washed with water, and dried to give the title compound (1.70 g, yield 98%).

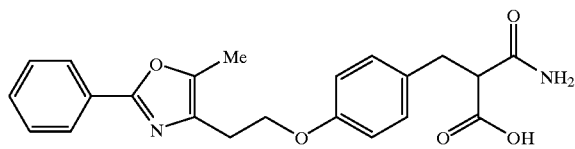

mp: 138.1–138.5° C.;

$^1$H-NMR(DMSO-$d_6$) δ ppm, 300 MHz: 2.35(3H, s), 2.92 (4H, m), 3.40(1H, t, J=5.6 Hz), 4.17(2H, t, J=5.0 Hz), 6.82(2H, d, J=6.5 Hz), 6.96(1H, brs), 7.09(2H, d, J=6.5 Hz), 7.40(1H, brs), 7.49(3H, m), 7.91(2H, m), 12.39(1H, brs).

EXAMPLE 4

2-Carbamoyl-3-[4-[2-(5-methyl-2-phenyl-4-oxazolyl)ethoxy]phenyl]propionic acid

4-[4-[2-(5-Methyl-2-phenyl-4-oxazolyl)ethoxy] benzilidene]-3,5-isooxazolidinedione (11.5 g, 29.3 mmol) synthesized according to the method described in WO95/18125 was dissolved in tetrahydrofuran (220 ml). 5% Palladium carbon (1.15 g) was added and the mixture was vigorously stirred under a hydrogen atmosphere (normal pressure) at room temperature for 13.5 hr. To the reaction mixture was added methanol (150 ml), and the catalyst was removed by celite filtration. The solvent was evaporated and the residue was suspended in 2.5N aqueous sodium hydroxide solution (50 ml) and washed with ethyl acetate. To the obtained aqueous layer was added 1N hydrochloride (150 ml) and the precipitated white solid was collected by filtration. The solid was washed with water and dried to give the title compound (5.10 g, yield 44%).

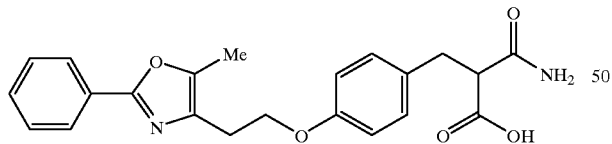

mp: 138.1–138.5° C.;

$^1$H-NMR (DMSO-$d_6$) δ ppm, 300 MHz: 2.35 (3H, s), 2.92 (4H, m), 3.40 (1H, t, J=5.6 Hz), 4.17 (2H, t, J=5.0 Hz), 6.82 (2H, d, J=6.5 Hz), 6.96 (1H, brs), 7.09 (2H, d, J=6.5 Hz), 7.40 (1H, brs), 7.49 (3H, m), 7.91 (2H, m), 12.39 (1H, brs).

EXAMPLE 5

2-[4-[2-(5-Methyl-2-phenyl-4-oxazolyl)ethoxy] benzyl]malonic acid

Dimethyl 2-[4-[2-(5-methyl-2-phenyl-4-oxazolyl)ethoxy] benzyl]malonate (6.00 g, 14.2 mmol) synthesized according to the method described in WO95/18125 was dissolved in methanol (60 ml) and tetrahydrofuran (30 ml). 2N Aqueous sodium hydroxide solution (17.7 ml, 35.5 mmol) was added at room temperature. The mixture was stirred for 68 hr and the solvent was evaporated. Water (100 ml) was added to the residue and acidified with 1N hydrochloric acid. The precipitated white solid was collected by filtration, washed with water and recrystallized from ethyl acetate-hexane to give the title compound (3.00 g, yield 53%) as a white powder.

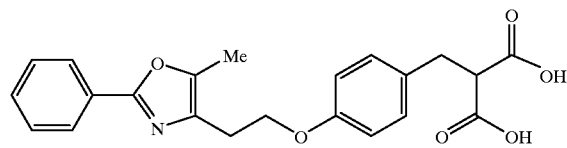

mp: 173.3–174.6° C.;

$^1$H-NMR (DMSO-$d_6$) δ ppm, 300 MHz: 2.34 (3H, s), 2.90 (4H, m), 3.49 (1H, d, J=8.0 Hz), 4.16 (2H, t, J=6.8 Hz), 6.83 (2H, d, J=8.4 Hz), 7.11 (2H, d, J=8.4 Hz), 7.47 (3H, m), 7.89 (2H, m),

EXAMPLE 6

Methyl 2-dimethylcarbamoyl-3-[4-[2-(5-methyl-2-phenyl-4-oxazolyl)ethoxy]phenyl]propionate In the same manner as in Example 2 using 2-methoxycarbonyl-3-[4-[2-(5-methyl-2-phenyl-4-oxazolyl)ethoxy]phenyl]propionic acid (5.00 g, 12.2 mmol) obtained in Example 1, the title compound was obtained as a yellow oil. Hexane-diethyl ether was added to the oil to solidify same to give the title compound (4.77 g, yield 89%).

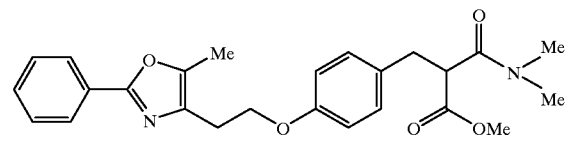

mp: 114.5–115.4° C.;

$^1$H-NMR (CDCl$_3$) δ ppm, 300 MHz: 2.37 (3H, s), 2.82 (3H, s), 2.90 (3H, s), 2.96 (2H, t, J=6.6 Hz), 3.17 (2H, d, J=7.8 Hz), 3.69 (3H, s), 3.83 (2H, t, J=7.4 Hz), 4.21 (2H, t, J=6.8 Hz), 6.80 (2H, d, J=8.4 Hz), 7.09 (2H, d, J=8.4 Hz), 7.42 (3H, m), 7.97 (2H, m).

EXAMPLE 7

2-Dimethylcarbamoyl-3-[4-[2-(5-methyl-2-phenyl-4-oxazolyl)ethoxy]phenyl]propionic acid (2.75 g, 6.31 mmol) obtained in Example 6 was dissolved in methanol (25 ml). Thereto was added 2.5 N aqueous sodium hydroxide solution (3.3 ml, 7.57 mmol) at room temperature. The mixture was stirred for 12 hr and the solvent was evaporated. Water was added to the residue and the aqueous layer was washed with ethyl acetate. Sodium chloride was added to the aqueous layer to saturate same. The mixture was acidified with 1N hydrochloric acid and extracted three times with ethyl acetate. The obtained organic layers were combined, dried over sodium sulfate and concentrated to dryness. Diethyl ether was added for solidification and the solid was collected by filtration to give the title compound (2.50 g, yield 94%) as a yellow-white solid.

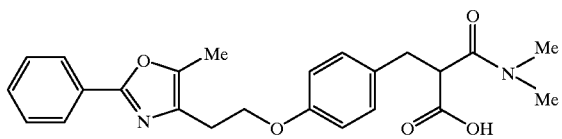

mp: 48.5–49.7° C.;

$^1$H-NMR (CDCl$_3$) δ ppm, 300 MHz: 2.38 (3H, s), 2.46 (3H, s), 2.89 (3H, s), 2.97 (2H, t, J=6.8 Hz), 3.10 (2H, dd, J=10.2 and 13.2 Hz), 3.25 (2H, dd, J=4.8 and 13.2 Hz), 3.78 (2H, dd, J=5.0 and 10.4 Hz), 4.22 (2H, t, J=6.8 Hz), 6.83 (2H, d, J=8.7 Hz), 7.06 (2H, d, J=8.7 Hz), 7.43 (3H, m), 7.97 (2H, m).

EXAMPLE 8

Methyl 2-methoxycarbonylcarbamoyl-3-[4-[2-(5-methyl-2-phenyl-4-oxazolyl)ethoxy]phenyl]propionate 2-Methoxycarbonyl-3-[4-[2-(5-methyl-2-phenyl-4-oxazolyl)ethoxy]phenyl]propionic acid (2.00 g, 4.89 mmol) obtained in Example 1 was dissolved in benzene (15 ml), and thionyl chloride (392 μl, 5.38 mmol) was added at room temperature. The mixture was refluxed under heating for 1.5 hr and the solvent was evaporated. The residue was dissolved in toluene (6 ml), and methyl carbamate (440 mg, 5.87 mmol) was added at room temperature. The mixture was stirred at 80–90° C. for 30 min. The solvent was evaporated and the resulting residue was purified by silica gel column chromatography (developing solvent; chloroform: methanol=30:1). The obtained white solid was recrystallized from methanol to give the title compound (1.40 g, yield 61%).

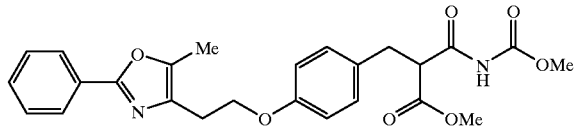

mp: 119.5–120.2° C.;

$^1$H-NMR (CDCl$_3$) δ ppm, 300 MHz: 2.36 (3H, s), 2.96 (2H, t, J=6.7 Hz), 3.19 (2H, m), 3.69 (3H, s), 3.74 (3H, s), 4.20 (2H, t, J=6.7 Hz), 4.32 (2H, t, J=7.9 Hz), 6.80 (2H, d, J=8.6 Hz), 7.13 (2H, d, J=8.6 Hz), 7.41 (3H, m), 7.92 (1H, brs), 7.97 (2H, m).

EXAMPLE 9

Dibenzyl 2-ethoxycarbonylmethyl-2-[4-[2-(5-methyl-2-phenyl-4-oxazolyl)ethoxy]benzyl]malonate Dibenzyl 2-[4-[2-(5-methyl-2-phenyl-4-oxazolyl)ethoxy]benzyl]malonate (26.0 g, 45.2 mmol) synthesized according to the method described in WO95/18125 was dissolved in tetrahydrofuran (250 ml), and sodium hydride (60% in oil, 2.2 g, 54.2 mmol) was added at 0° C., which was followed by stirring at room temperature for 30 min. To the reaction mixture was added a solution of ethyl bromoacetate (15.3 ml, 135.6 mmol) in tetrahydrofuran (50 ml) at room temperature. After stirring for 1 hr, sodium hydride (60% in oil, 1.1 g, 27.1 mmol) and ethyl bromoacetate (5.1 ml, 45.2 mmol) were added. After stirring for 1 hr, sodium hydride (60% in oil, 2.2 g, 54.2 mmol) was added and the mixture was stirred for 1 hr. Water and 1N aqueous sodium hydrogensulfate solution were added to the reaction mixture and extracted three times with ethyl acetate (200 ml). The extracted organic layers were combined, washed with brine, dried over sodium sulfate and concentrated. The residue was purified by silica gel column chromatography (developing solvent; hexane:ethyl acetate=5:1→3:1) to give the title compound (30.2 g, yield 100%) as an oil.

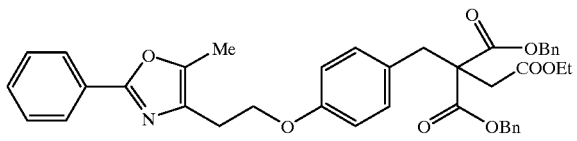

$^1$H-NMR (CDCl$_3$) δ ppm, 300 MHz: 1.20 (3H, q, J=7.1 Hz), 2.36 (3H, s), 2.85 (2H, s), 2.95 (2H, t, J=6.7 Hz), 3.33 (2H, s), 4.07 (2H, q, J=7.1 Hz), 4.18 (2H, t, J=6.7 Hz), 5.10 (1H, d, J=13.1 Hz), 5.12 (1H, d, J=13.1 Hz), 6.69 (2H, d, J=8.7 Hz), 6.85 (2H, d, J=8.7 Hz), 7.20–7.33 (10H, m), 7.41 (3H, m), 7.98 (2H, m).

EXAMPLE 10

2-Ethoxycarbonylmethyl-2-[4-[2-(5-methyl-2-phenyl-4-oxazolyl)ethoxy]benzyl]malonic acid Dibenzyl 2-ethoxycarbonylmethyl-2-[4-[2-(5-methyl-2-phenyl-4-oxazolyl)ethoxy]benzyl]malonate (29.5 g, 44.6 mmol) obtained in Example 9 was dissolved in methanol (150 ml) and tetrahydrofuran (150 ml), and 5% palladium carbon (2.0 g) was added. The mixture was vigorously stirred at room temperature under a hydrogen atmosphere (3.3–3.4 atm) for 6 hr. After stirring, the catalyst was removed with celite and the solvent was evaporated to give the title compound (21.0 g, yield 98%) as an orange-yellow solid.

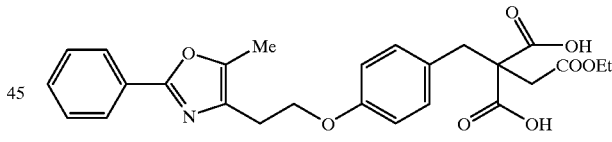

$^1$H-NMR (CDCl$_3$) δ ppm, 300 MHz: 1.17 (3H, q, J=7.1 Hz), 2.41 (3H, s), 3.03 (2H, t, J=6.0 Hz), 3.14 (2H, s), 3.20 (2H, s), 4.07 (2H, q, J=7.1 Hz), 4.15 (2H, t, J=6.0 Hz), 6.77 (2H, d, J=8.3 Hz), 7.07 (2H, d, J=8.3 Hz), 7.45 (3H, m), 7.94 (2H, m), 8.03 (1H, brs)

EXAMPLE 11

2-Ethoxycarbonylmethyl-3-[4-[2-(5-methyl-2-phenyl-4-oxazolyl)ethoxy]phenyl]propionic acid 2-Ethoxycarbonylmethyl-2-[4-[2-(5-methyl-2-phenyl-4-oxazolyl)ethoxy]benzyl]malonic acid (21.0 g, 43.7 mmol) obtained in Example 10 was heated at 150° C. for 30 min. The reaction mixture was purified by silica gel column chromatography (developing solvent; chloroform: methanol=40:1→20:1) to give the title compound (15.0 g, yield 79%) as a yellow-brown oil.

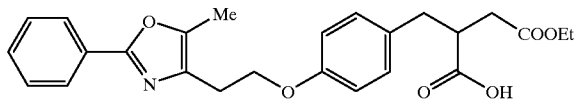
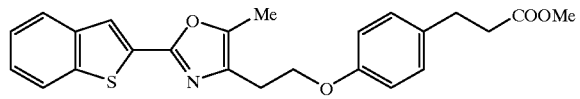

¹H-NMR (CDCl₃) δ ppm, 300 MHz: 1.21 (3H, t, J=7.1 Hz), 2.37 (3H, s), 2.38 (1H, dd, J=4.8 and 16.8 Hz), 2.55–2.78 (2H, m), 2.90–3.17 (4H, m), 4.09 (2H, q, J=7.1 Hz), 4.20 (2H, t, J=6.6 Hz), 6.82 (2H, d, J=8.6 Hz), 7.07 (2H, d, J=8.6 Hz), 7.44 (3H, m), 7.97 (2H, m).

EXAMPLE 12

Ethyl 3-carbamoyl-4-[4-[2-(5-methyl-2-phenyl-4-oxazolyl)ethoxy]phenyl]butyrate

To 2-ethoxycarbonylmethyl-3-[4-[2-(5-methyl-2-phenyl-4-oxazolyl)ethoxy]phenyl]propionic acid (4.5 g, 10.3 mmol) obtained in Example 11 was added thionyl chloride (30 ml, 411.3 mmol) and the mixture was refluxed under heating for 1 hr at 40° C. The reaction mixture was concentrated and tetrahydrofuran (25 ml) was added to the residue. 28% Aqueous ammonia (15 ml) was added at 0° C. and the mixture was stirred for 10 min. The mixture was acidified with 1N sodium hydrogensulfate and the precipitated solid (2.93 g) was collected by filtration. A part (1.30 g) thereof was recrystallized from ethyl acetate to give the title compound (0.70 g, yield 35%).

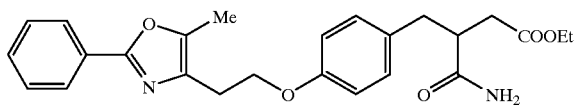

mp: 141.8–142.3° C.; ¹H-NMR (CDCl₃) δ ppm, 300 MHz: 1.23 (3H, q, J=7.2 Hz), 2.38 (3H, s), 2.42 (1H, dd, J=3.8 and 16.7 Hz), 2.60–2.90 (4H, m), 2.97 (2H, t, J=6.5 Hz), 4.10 (2H, q, J=7.2 Hz), 5.20 (1H, brs), 5.44 (1H, brs), 6.83 (2H, d, J=9.0 Hz), 7.09 (2H, d, J=9.0 Hz), 7.43 (3H, m), 7.97 (2H, m).

EXAMPLE 13

Methyl 3-[4-[2-(2-(benzothiophen-2-yl)-5-methyl-4-oxazolyl)ethoxy]phenyl]propionate Dimethyl 2-[4-[2-(5-methyl-2-phenyl-4-oxazolyl)ethoxy]benzyl]malonate (2.83 g, 5.91 mmol) synthesized according to the method described in WO95/18125 was dissolved in dimethyl sulfoxide (25 ml), and lithium chloride (500 mg, 11.82 mmol) and water (212 μl, 11.82 mmol) were added at room temperature. The mixture was refluxed under heating for 45 min and cooled to room temperature. Water (50 ml) was added and the mixture was extracted three times with ethyl acetate (50 ml). The extracted organic layers were combined, dried over sodium sulfate and concentrated. The residue was purified by silica gel column chromatography (developing solvent; hexane:ethyl acetate=5:1) to give the title compound (1.98 g, yield 80%).

¹H-NMR (CDCl₃) δ ppm, 300 MHz: 2.39 (3H, s), 2.58 (2H, t, J=7.4 Hz), 2.88 (2H, t, J=7.8 Hz), 2.97 (2H, m), 3.65 (2H, s), 4.21 (2H, q, J=6.6 Hz), 6.82 (2H, d, J=8.7 Hz), 7.09 (2H, d, J=8.7 Hz), 7.37 (2H, m), 7.75–7.87 (3H, m).

EXAMPLE 14

3-[4-[2-(2-(Benzothiophen-2-yl)-5-methyl-4-oxazolyl)ethoxy]phenyl]propionic acid Methyl 3-[4-[2-(2-(benzothiophen-2-yl)-5-methyl-4-oxazolyl)ethoxy]phenyl]propionate (1.90 g, 4.51 mmol) obtained in Example 13 was dissolved in methanol (20 ml) and tetrahydrofuran (30 ml), and 2.5N aqueous sodium hydroxide solution (2.2 ml, 5.5 mmol) was added at room temperature, which was followed by stirring for 13 hr. Then, the solvent was evaporated and water was added to the obtained residue. 1N Hydrochloric acid was added to acidify the solution and the precipitated white solid was collected by filtration, washed with water and dried to give the title compound (1.80 g, yield 98%) as a white solid.

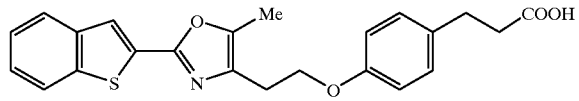

¹H-NMR (DMSO-d₆) δ ppm, 300 MHz: 2.37 (3H, s), 2.46 (2H, d, J=7.2 Hz), 2.73 (2H, d, J=7.7 Hz), 2.91 (2H, d, J=6.3 Hz), 4.16 (2H, t, J=6.6 Hz), 6.84 (2H, d, J=8.7 Hz), 7.11 (2H, d, J=8.7 Hz), 7.43 (2H, m), 7.85–8.05 (3H, m), 12.07 (1H, brs).

EXAMPLE 15

N-[3-[4-[2-(2-(Benzothiophen-2-yl)-5-methyl-4-oxazolyl)ethoxy]phenyl]propionyl]urea To 3-[4-[2-(2-(benzothiophen-2-yl)-5-methyl-4-oxazolyl)ethoxy]phenyl]propionic acid (850 mg, 2.09 mmol) obtained in Example 14 was added thionyl chloride (2 ml, 27.4 mmol) and the mixture was stirred under heating for 40 min at 60° C. The reaction mixture was concentrated and N,N-dimethylaniline (10 ml) was added to the residue. Urea (250 mg, 4.17 mmol) was added and the mixture was stirred under heating for 5 hr at 150° C. Urea (250 mg, 4.17 mmol) was again added and the mixture was heated for 10 hr at 150° C. The reaction mixture was cooled to room temperature and the precipitated solid (468 mg) was collected by filtration. A part (260 mg) thereof was washed successively with water, ethyl acetate/tetrahydrofuran (9:1), 10% aqueous sodium hydroxide solution, 1N hydrochloric acid, water and tetrahydrofuran, and dried to give the title compound (110 mg, yield 21%) as a gray-white solid.

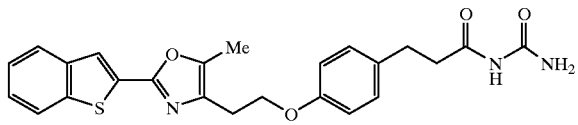

mp: 241.3–241.9° C.;

¹H-NMR (DMSO-d₆) δ ppm, 300 MHz: 2.37 (3H, s), 2.53 (2H, d, J=7.8 Hz), 2.75 (2H, d, J=7.5 Hz), 2.91 (2H, d, J=6.6 Hz), 4.16 (2H, t, J=6.3 Hz), 6.85 (2H, d, J=8.7 Hz), 7.10 (2H, d, J=8.7 Hz), 7.16 (1H, brs), 7.43 (2H, m), 7.72 (1H, brs), 7.89–8.05 (3H, m), 10.11 (1H, brs).

EXAMPLE 16

Methyl 3-[4-[2-(5-methyl-2-phenyl-4-oxazolyl) ethoxy]phenyl]propionate

Sodium hydride (60% in oil, 2.11 g, 88.1 mmol) was washed twice with n-hexane (10 ml) under a nitrogen atmosphere, suspended in N,N-dimethylformamide (50 ml) and ice-cooled. To this solution was added methyl 3-(p-hydroxyphenyl)propionate (15.9 g, 88.1 mol) over 15 min. After 10 min when hydrogen bubbling finished, a solution of ethyl 2-(5-methyl-2-phenyl-4-oxazolyl)-p-toluenesulfonate (20.0 g, 56.0 mmol) in N,N-dimethylformamide (50 ml) was added. The mixture was stirred at room temperature for 5 hr, and ethyl aceate (500 ml) and 1N aqueous sodium hydroxide solution (200 ml) were added for partition. The obtained organic layer was washed with 1N hydrochloric acid (100 ml), saturated aqueous sodium hydrogencarbonate solution (100 ml) and saturated brine (100 ml), dried over magnesium sulfate and concentrated under reduced pressure. The residue was purified by silica gel column chromatography (developing solvent; n-hexane:ethyl acetate=85:15) to give the title compound (14.0 g, yield 68%) as a white solid.

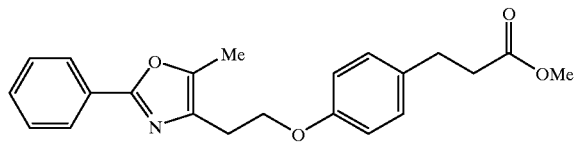

mp: 50.2–51.7° C.;

¹H-NMR (CDCl₃) δ ppm, 300 MHz: 2.37 (3H, s), 2.58 (2H, t, J=7.5 Hz), 2.88 (2H, t, J=7.5 Hz), 2.96 (2H, t, J=6.7 Hz), 3.65 (3H, s), 4.22 (2H, t, J=6.7 Hz), 6.82 (2H, d, J=8.6 Hz), 7.08 (2H, d, J=8.6 Hz), 7.41 (3H, m), 7.96 (2H, m);

Elemental Analysis: Calculated (%) C;72.31, H;6.34, N;3.83; Found (%) C;72.13, H;6.32, N;3.66.

EXAMPLE 17

3-[4-[2-(5-Methyl-2-phenyl-4-oxazolyl)ethoxy] phenyl]propionic acid

Methyl 3-[4-[2-(5-methyl-2-phenyl-4-oxazolyl)ethoxy] phenyl]propionate (13.0 g, 35.6 mmol) obtained in Example 16 was dissolved in methanol (400 ml), and 1N aqueous sodium hydroxide solution (50 ml) was added with stirring at room temperature. After stirring for 15 hr, the solvent was evaporated under reduced pressure. Ethyl acetate (50 ml) and water (200 ml) were added for partition. 1N Hydrochloric acid was added to the aqueous layer to acidify same. The precipitated solid was collected by filtration, washed with water (50 ml) and dried under reduced pressure to give the title compound (12.0 g, yield 96%) as a white solid.

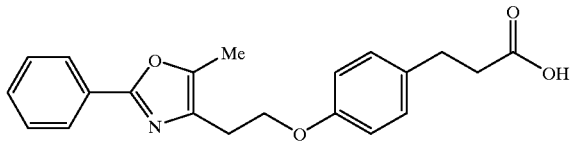

mp: 141.8–144.0° C.;

¹H-NMR (CDCl₃) δ ppm, 300 MHz: 2.37 (3H, s), 2.62 (2H, t, J=7.5 Hz), 2.89 (2H, t, J=7.5 Hz), 2.97 (2H, t, J=6.7 Hz), 4.21 (2H, t, J=6.7 Hz), 6.82 (2H, d, J=8.6 Hz), 7.09 (2H, d, J=8.6 Hz), 7.41 (3H, m), 7.96 (2H, m);

Elemental Analysis: Calculated (X) C;71.05, H;6.08, N;3.95; Found (X) C;71.22, H;5.83, N;3.63.

EXAMPLE 18

3-[4-[2-(5-Methyl-2-phenyl-4-oxazolyl)ethoxy] phenyl]propionamide

Methyl 3-[4-[2-(5-methyl-2-phenyl-4-oxazolyl)ethoxy] phenyl]propionate (600 mg, 1.64 mmol) obtained in Example 16 was added to ammonia/methanol (50 ml), and the mixture was stirred for 24 hr at room temperature. The solvent was evaporated under reduced pressure. Ethyl acetate (50 ml) and 1N aqueous sodium hydroxide solution (50 ml) were added for partition. The organic layer was washed with water (50 ml) and saturated brine (50 ml), dried over magnesium sulfate, and concentrated under reduced pressure to give the title compound (464 mg, yield 80%) as a white solid.

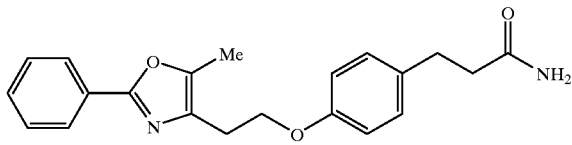

mp: 139.2–140.0° C.;

¹H-NMR (CDCl₃) δ ppm, 300 MHz: 2.37 (3H, s), 2.48 (2H, t, J=7.5 Hz), 2.90 (2H, t, J=7.5 Hz), 2.97 (2H, t, J=6.7 Hz), 4.22 (2H, t, J=6.7 Hz), 5.20 (2H, brs), 6.82 (2H, d, J=8.5 Hz), 7.10 (2H, d, J=8.5 Hz), 7.41 (3H, m), 7.96 (2H, m);

Elemental Analysis: Calculated (%) C;71.98, H;6.33, N;7.99; Found (%) C;72.02, H;6.20, N;7.67.

EXAMPLE 19

Methyl N-[3-[4-[2-(5-methyl-2-phenyl-4-oxazolyl) ethoxy]phenyl]propionyl]carbamide To 3-[4-[2-(5-methyl-2-phenyl-4-oxazolyl)ethoxy] phenyl]propionic acid (1.00 g, 2.85 mmol) obtained in Example 17 was added thionyl chloride (1.7 ml), and the mixture was stirred under heating for 1 hr at 100° C. Excess thionyl chloride was evaporated under reduced pressure and the obtained residue was dissolved in benzene (2.3 ml). Thereto was added methyl carbamate (214 mg, 2.85 mmol) and the mixture was stirred under heating for 5 hr at 80° C. Water (10 ml) and ethyl acetate (50 ml) were added for partition. The organic layer was washed with saturated brine (20 ml), dried over magnesium sulfate, and concentrated under reduced pressure. The residue was purified by silica gel column chromatography (developing solvent; dichloromethane: methanol=100:1) to give the title compound (433 mg, yield 37%) as a white solid.

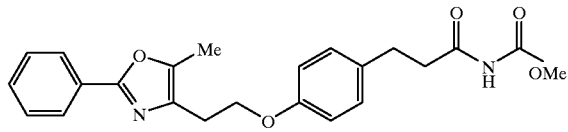

mp: 127.7–132.3° C.;

¹H-NMR (CDCl₃) δ ppm, 300 MHz: 2.36 (3H, s), 2.87–3.05 (6H, m), 3.74 (3H, s), 4.21 (2H, t, J=6.7 Hz), 6.82 (2H, d, J=8.6 Hz), 7.11 (2H, d, J=8.6 Hz), 7.40 (3H, m), 7.65 (1H, brs), 7.97 (2H, m);

Elemental Analysis: Calculated (%) C;67.63, H;5.92, N;6.86; Found (%) C;64.96, H;5.51, N;6.14.

EXAMPLE 20

N-[3-[4-[2-(5-Methyl-2-phenyl-4-oxazolyl)ethoxy]phenyl]propionyl]urea

To 3-[4-[2-(5-methyl-2-phenyl-4-oxazolyl)ethoxy]phenyl]propionic acid (1.00 g, 2.85 mmol) obtained in Example 17 was added thionyl chloride (1.7 ml), and the mixture was stirred under heating for 1 hr at 100° C. Excess thionyl chloride was evaporated under reduced pressure and urea (257 mg, 4.28 mmol) was added to the obtained residue. The mixture was stirred under heating for 1 hr at 120° C. and purified by silica gel column chromatography (developing solvent; dichloromethane: methanol=10:1) to give the title compound (560 mg, yield 50%) as a white solid.

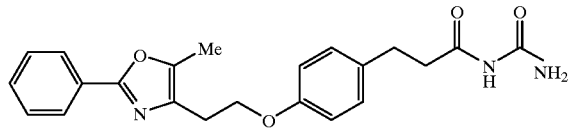

mp: 177.1–178.0° C.;

¹H-NMR (CDCl₃) δ ppm, 300 MHz: 2.37 (3H, s), 2.58 (2H, t, J=7.9 Hz), 2.90 (2N, t, J=7.9 Hz), 2.96 (2H, t, J=6.7 Hz), 4.21 (2H, t, J=6.7 Hz), 5.27 (1H, brs), 6.82 (2H, d, J=8.6 Hz), 7.08 (2H, d, J=8.6 Hz), 7.40 (3H, m), 7.96 (2H, m), 8.16 (1H, brs), 8.56 (1H, brs);

Elemental Analysis: Calculated (%) C;67.16, H;5.89, N;10.68; Found (%) C;64.79, H;5.18, N;8.95.

EXAMPLE 21

N-Acetyl-3-[4-[2-(5-methyl-2-phenyl-4-oxazolyl)ethoxy]phenyl]propionamide

To 3-[4-[2-(5-methyl-2-phenyl-4-oxazolyl)ethoxy]phenyl]propionic acid (1.50 g, 4.27 mmol) obtained in Example 17 was added thionyl chloride (2.0 ml), and the mixture was stirred under heating for 1 hr at 100° C. Excess thionyl chloride was evaporated under reduced pressure and acetamide (504 mg, 8.54 mmol) was added to the obtained residue. The mixture was stirred under heating for 1 hr at 120° C. Methanol (5 ml) was added, and the reaction mixture was stirred for 10 min and concentrated under reduced pressure. The obtained residue was purified by silica gel column chromatography (developing solvent; n-hexane:ethyl acetate=1:1) to give the title compound (541 mg, yield 32%) as a white solid.

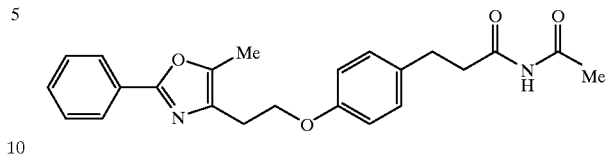

mp: 127.7–128.7° C.;

¹H-NMR (CDCl₃) δ ppm, 300 MHz: 2.33 (3H, s), 2.38 (3H, s), 2.78 (2H, t, J=6.2 Hz), 2.91 (2H, t, J=6.2 Hz), 2.98 (2H, t, J=6.6 Hz), 4.22 (2H, t, J=6.6 Hz), 6.83 (2H, d, J=8.6 Hz), 7.10 (2H, d, J=8.6 Hz), 7.40 (3H, m), 7.98 (2H, m).

EXAMPLE 22

S-Methyl-3-[4-[2-(5-methyl-2-phenyl-4-oxazolyl)ethoxy]phenyl]propionyl]thiocarbamate To 3-[4-[2-(5-methyl-2-phenyl-4-oxazolyl)ethoxy]phenyl]propionic acid (5.00 g, 14.2 mmol) obtained in Example 17 was added methyl thioisocyanate (1.56 g, 21.4 mmol) and trifluoroacetic acid (5.5 ml, 71.2 mmol), and the mixture was stirred under heating for 3 days at 60° C. Ethyl acetate (150 ml) and water (50 ml) were added for partition. The organic layer was washed with 1N aqueous sodium hydroxide solution (100 ml) and saturated brine (50 ml), dried over magnesium sulfate and concentrated under reduced pressure. The obtained residue was purified by silica gel column chromatography (developing solvent; dichloromethane:methanol=99:1) and washed with ethyl acetate (20 ml) to give the title compound (1.23 g, yield 20%) as a white solid.

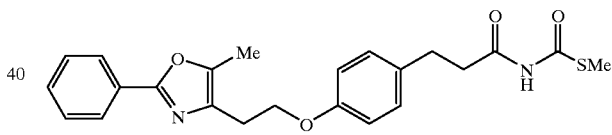

mp: 127.8–128.3° C.;

¹H-NMR (CDCl₃) δ ppm, 300 MHz: 2.33 (3H, s), 2.37 (3H, s), 2.76 (2H, t, J=7.5 Hz), 2.95 (4H, m), 4.22 (2H, t, J=6.7 Hz), 6.82 (2H, d, J=8.6 Hz), 7.09 (2H, d, J=8.6 Hz), 7.40 (3H, m), 7.96 (2H, m), 8.09 (1H, brs);

Elemental Analysis: Calculated (%) C;65.07, H;5.70, N;6.60; Found (%) C;65.06, H;5.54, N;6.63.

EXAMPLE 23

2 Carbamoyl-3-[4-[2-[2-(benzothiophen-2-yl)-5-methyl-4-oxazolyl)ethoxy]phenyl]propionic acid 5-[4-[2-[2-(Benzothiophen-2-yl)-5-methyl-4-oxazolyl)ethoxy]benzyl]isoxazolidine-3,5-dione (1.80 g, 4.01 mmol) synthesized according to the method described in WO95/18125 was dissolved in tetrahydrofuran (50 ml), and hydrogenated (3.5 atm) at room temperature in the presence of 5% palladium carbon (0.18 g). After 4 hours, the catalyst was removed and the filtrate was concentrated under reduced pressure, and the obtained residue was washed with diethyl ether (20 ml) to give the title compound (1.55 g, yield 86%) as a white solid.

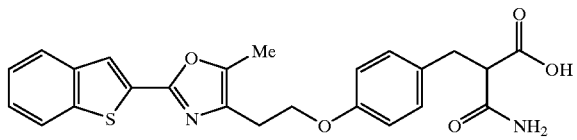

mp: 148.2–149.0° C. (decomposition);
$^1$H-NMR (DMSO-$d_6$) δ ppm, 300 MHz: 2.36 (3H, s), 2.85–2.95 (4H, m), 3.39 (1H, t, J=7.5 Hz), 4.15 (2H, t, J=6.6 Hz), 6.82 (2H, d, J=8.4 Hz), 6.96 (1H, brs), 7.09 (2H, d, J=8.4 Hz), 7.40–7.45 (3H, m), 7.90–8.10 (3H, m).

EXAMPLE 24

2-[4-[2-(5-Methyl-2-phenyl-4-oxazolyl)ethoxy]benzyl]malonamide

Dimethyl 2-[4-[2-(5-methyl-2-phenyl-4-oxazolyl)ethoxy]benzyl]malonate (3.00 g, 7.08 mmol) synthesized according to the method described in WO95/18125 was dissolved in methanol-tetrahydrofuran (1:1, 100 ml), and 28% aqueous ammonia (20 ml) was added, which was followed by stirring for 5 days at room temperature. Thereto was added 1N aqueous sodium hydroxide solution (30 ml) and the mixture was stirred for 1 hr. The solvent was evaporated under reduced pressure, and the obtained residue was partitioned between tetrahydrofuran-ethyl acetate (1:1, 100 ml) and water (50 ml). The organic layer was washed with saturated brine (50 ml), dried over magnesium sulfate and concentrated under reduced pressure to give the title compound (2.50 g, yield 90%) as a white solid.

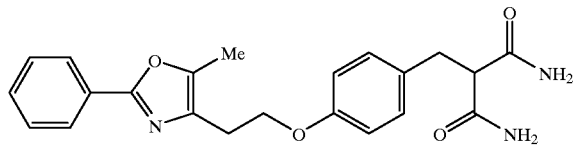

mp: 222.5–223.4° C. (decomposition);
$^1$H-NMR (DMSO-$d_6$) δ ppm, 300 MHz: 2.34 (3H, s), 2.80–2.92 (4H, m), 3.22 (1H, t, J=7.5 Hz), 4.15 (2H, t, J=6.7 Hz), 6.81 (2H, d, J=8.4 Hz), 6.96 (2H, brs), 7.07 (2H, d, J=8.4 Hz), 7.19 (2H, brs), 7.48 (3H, m), 7.90 (2H, m).

EXAMPLE 25

Methyl N-acetyl-2-carbamoyl-3-[4-[2-(5-methyl-2-phenyl-4-oxazolyl)ethoxy]phenyl]propionate Thionyl chloride (1.0 ml) was added to 2-methoxycarbonyl-3-[4-[2-(5-methyl-2-phenyl-4-oxazolyl)ethoxy]phenyl]propionic acid (2.63 g, 6.43 mmol) obtained in Example 1, and the mixture was stirred with heating at 60° C. for 1 hr. Excess thionyl chloride was evaporated under reduced pressure and acetamide (504 mg, 8.54 mmol) was added to the residue. The mixture was stirred with heating at 120° C. for 30 min. Tetrahydrofuran-ethyl acetate (1:1, 100 ml) and water (50 ml) were added to the reaction mixture for partition. The organic layer was washed with saturated brine (50 ml), dried over magnesium sulfate and concentrated under reduced pressure. The obtained residue was purified by silica gel column chromatography (developing solvent; n-hexane:ethyl acetate=1:1) to give the title compound (1.08 g, yield 34%) as a white solid.

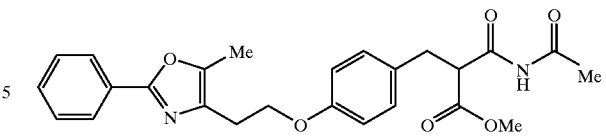

mp: 126.5–127.9° C.;
$^1$H-NMR (CDCl$_3$) δ ppm, 300 MHz: 2.33 (3H, s), 2.36 (3H, s), 2.96 (2H, t, J=6.6 Hz), 3.16 (2H, d, J=7.2 Hz), 3.69 (3H, s), 3.78 (1H, t, J=7.2 Hz), 4.20 (2H, t, J=6.6 Hz), 6.81 (2H, d, J=8.7 Hz), 7.08 (2H, d, J=8.7 Hz), 7.40 (3H, m), 7.97 (2H, m), 8.58 (1H, brs).

EXAMPLE 26

2-Methoxycarbonyl-2-methyl-3-[4-[2-(5-methyl-2-phenyl-4-oxazolyl)ethoxy]phenyl]propionic acid To a solution of 2-methoxycarbonyl-3-[4-[2-(5-methyl-2-phenyl-4-oxazolyl)ethoxy]phenyl]propionic acid (4.10 g, 10.0 mmol) obtained in Example 1 in tetrahydrofuran (50 ml) was dropwise added lithium diisopropylamide (1.5 M cyclohexane solution, 15.0 ml, 22.5 mmol) at −78° C. under argon atmosphere. The mixture was stirred at said temperature and methyl iodide (2.5 ml, 40 mmol) was dropwise added. The mixture was stirred at said temperature for 2 hr and 10% aqeuous ammonium chloride (20 ml) was added. The organic layer was separated and the aqueous layer was extracted with ethyl acetate (50 ml). The obtained organic layers were combined, washed with saturated brine (10 ml), dried over magnesium sulfate and concentrated under reduced pressure to give the crude title compound (4.78 g).

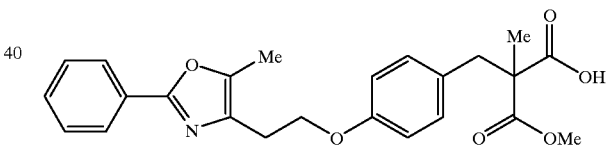

EXAMPLE 27

Methyl 2-carbamoyl-2-methyl-3-[4-[2-(5-methyl-2-phenyl-4-oxazolyl)ethoxy]phenyl]propionate Thionyl chloride (1.0 ml) was added to crude 2-methoxycarbonyl-2-methyl-3-[4-[2-(5-methyl-2-phenyl-4-oxazolyl)ethoxy]phenyl]propionic acid (4.60 g) obtained in Example 26, and the mixture was stirred with heating at 60° C. for 1 hr. Excess thionyl chloride was evaporated under reduced pressure and the residue was dissolved in acetone (10 ml), which was dropwise added to 28% aqueous ammonia (20 ml). After stirring at room temperature for 30 min, ethyl acetate (100 ml) was added for partition. The organic layer was washed with saturated brine (50 ml), dried over magnesium sulfate and concentrated under reduced pressure. The obtained residue was purified by silica gel column chromatography (developing solvent; n-hexane:ethyl acetate=2:3) to give the title compound (1.22 g, yield 28%) as a white solid.

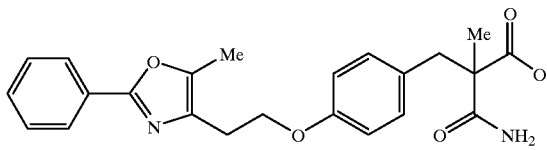

¹H-NMR (CDCl₃) δ ppm, 300 MHz: 1.41 (3H, s), 2.36 (3H, s), 2.96 (2H, t, J=6.5 Hz), 3.03 (1H, d, J=13.5 Hz), 3.27 (1H, d, J=13.5 Hz), 3.71 (3H, s), 4.21 (2H, t, J=6.5 Hz), 5.43 (1H, brs), 6.78 (2H, d, J=9.0 Hz), 6.86 (1H, brs), 7.02 (2H, d, J=9.0 Hz), 7.43 (3H, m), 7.97 (2H, m).

EXAMPLE 28

2-Carbamoyl-2-methyl-3-[4-[2-(5-methyl-2-phenyl-4-oxazolyl)ethoxy]phenyl]propionic acid Methyl 2-carbamoyl-2-methyl-3-[4-[2-(5-methyl-2-phenyl-4-oxazolyl)ethoxy]phenyl]propionate (1.17 g, 2.77 mmol) obtained in Example 27 was dissolved in methanol-tetrahydrofuran (1:1, 20 ml). 1N Aqueous sodium hydroxide solution (10 ml) was added and the mixture was stirred at room temperature for 1 hr. 1N Hydrochloric acid was added to acidify the reaction mixture, and water (50 ml) and ethyl acetate (150 ml) were added for partition. The organic layer was washed with saturated brine (50 ml), dried over magnesium sulfate and concentrated under reduced pressure to give the title compound (1.02 g, yield 90%) as a white solid.

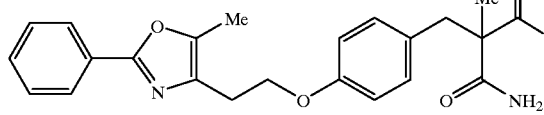

mp: 150.5–151.5° C. (decomposition);

¹H-NMR (DMSO-d₆) δ ppm, 300 MHz: 1.12 (3H, s), 2.35 (3H, s), 2.91 (2H, t, J=6.6 Hz), 3.00 (2H, s) 4.17 (2H, t, J=6.6 Hz), 6.82 (2H, d, J=8.7 Hz), 7.06 (2H, d, J=8.7 Hz), 7.14 (1H, brs), 7.22 (1H, brs), 7.49 (3H, m), 7.90 (2H, m), 12.36 (1H, brs).

EXAMPLE 29

N-[2-Methoxycarbonyl-3-[4-[2-(5-methyl-2-phenyl-4-oxazolyl)ethoxy]phenyl]propionyl]urea Thionyl chloride (4.0 ml) was added to 2-methoxycarbonyl-3-[4-(2-(5-ethyl-2-phenyl-4-oxazolyl)ethoxy]phenyl]propionic acid (4.10 g, 10.0 mmol) obtained in Example 1 and the mixture was stirred with heating at 60° C. for 1 hr. Excess thionyl chloride was evaporated under reduced pressure and urea (900 mg, 15.0 mmol) was added to the residue obtained, which was followed by stirring with heating at 100° C. for 45 min. Chloroform (100 ml) and water (50 ml) were added for partition. The organic layer was washed with saturated brine (50 ml), dried over magnesium sulfate and concentrated under reduced pressure. The obtained residue was purified by silica gel column chromatography (developing solvent; n-hexane:ethyl acetate=1:1) to give the title compound (3.71 g, yield 82%) as a white solid.

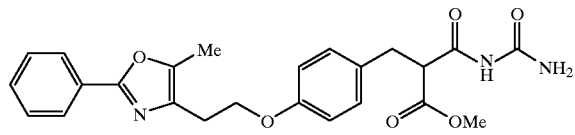

mp: 74.6–75.6° C.;

¹H-NMR (CDCl₃) δ ppm, 300 MHz: 2.36 (3H, s), 2.95 (2H, d, J=6.6 Hz), 3.16 (2H, d, J=7.2 Hz), 3.55 (1H, t, J=7.2 Hz), 3.68 (3H, s), 4.20 (2H, t, J=6.6 Hz), 5.32 (1H, brs), 6.81 (2H, d, J=8.4 Hz), 7.06 (2H, d, J=8.4 Hz), 7.41 (3H, m), 7.96 (2H, m), 8.01 (1H, brs), 8.80 (1H, brs).

EXAMPLE 30

N,N'-Dimethyl-2-[4-[2-(5-methyl-2-phenyl-4-oxazolyl)ethoxy]benzyl]malonamide

Dimethyl 2-[4-[2-(5-methyl-2-phenyl-4-oxazolyl)ethoxy]benzyl]malonate (3.00 g, 7.08 mmol) synthesized according to the method described in WO95/18125 was dissolved in methanol-tetrahydrofuran (1:1, 100 ml), and 40% aqueous methylamine solution (50 ml) was added. The mixture was stirred at room temperature for 1 hr. The reaction mixture was concentrated under reduced pressure and the obtained residue was recrystallized from methanol (500 ml) to give the title compound (1.80 g, yield 60%) as a white solid.

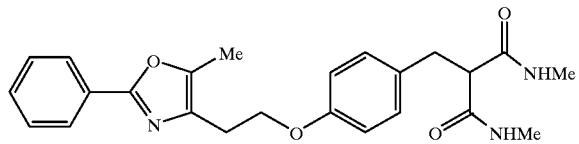

mp: 217.2–218.8° C.;

¹H-NMR (DMSO-d₆) δ ppm, 300 MHz: 2.31 (3H, s), 2.45 (3H, s), 2.50 (31H, s), 2.87 (4H, m), 3.15 (1H, t, J=7.2 Hz), 4.12 (2H, t, J=6.6 Hz), 6.78 (21H, d, J=8.4 Hz), 7.01 (2H, d, J=8.4 Hz), 7.46 (3H, m), 7.64 (2H, m), 7.87 (2H, m).

EXAMPLE 31

Methyl 2-methylcarbamoyl-3-[4-[2-(5-methyl-2-phenyl-4-oxazolyl)ethoxy]phenyl]propionate Dimethyl 2-[4-[2-(5-methyl-2-phenyl-4-oxazolyl)ethoxy]benzyl]malonate (3.00 g, 7.08 mmol) synthesized according to the method described in WO95/18125 was dissolved in methanol-tetrahydrofuran (1:1, 100 ml), and 40% aqueous methylamine solution (50 ml) was added. The mixture was stirred at room temperature for 0.5 hr. The reaction mixture was concentrated under reduced pressure, and the obtained residue was purified by silica gel column chromatography (developing solvent; n-hexane:ethyl acetate=1:2) to give the title compound (1.50 g, yield 50%) as a white solid.

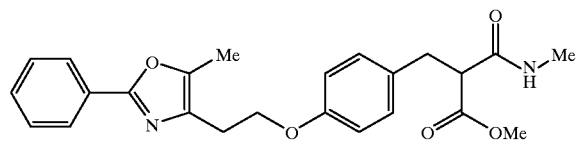

mp: 151.2–151.8° C.;

¹H-NMR (CDCl₃) δ ppm, 300 MHz: 2.36 (3H, s), 2.77 (3H, d, J=4.5 Hz), 2.96 (2H, d, J=6.6 Hz), 3.16 (2H, m), 3.42

(1H, dd, J=6.0 and 7.8 Hz), 3.63 (3H, s), 4.20 (2H, t, J=6.6 Hz), 6.35 (1H, brd), 6.80 (2H, d, J=8.7 Hz), 7.05 (2H, d, J=8.7 Hz), 7.41 (3H, m), 7.98 (2H, m)

EXAMPLE 32

2-Methylcarbamoyl-3-[4-[2-(5-methyl-2-phenyl-4-oxazolyl)ethoxy]phenyl]propionic acid Methyl 2-methylcarbamoyl-3-[4-[2-(5-methyl-2-phenyl-4-oxazolyl)ethoxy]phenyl]propionate (1.50 g, 3.55 mmol) obtained in Example 31 was dissolved in methanol-tetrahydrofuran (1:1, 40 ml) and 1N aqueous sodium hydroxide solution (20 ml) was added. The mixture was stirred at room temperature for 1 hr. 1N Hydrochloric acid was added to acidify the reaction mixture, and water (50 ml) and ethyl acetate (100 ml) were added for partition. The organic layer was washed with saturated brine (50 ml), dried over magnesium sulfate and concentrated under reduced pressure to give the title compound (1.40 g, yield 96%) as a white solid.

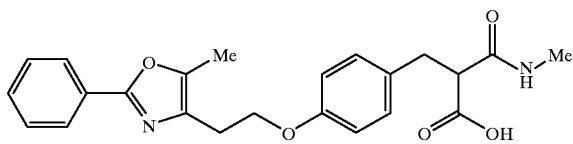

mp: 145.7–146.8° C. (decomposition);

$^1$H-NMR (DMSO-$d_6$) δ ppm, 300 MHz: 2.33 (3H, s), 2.47 (3H, s), 2.88 (4H, m), 3.35 (1H, dd, J=8.4 and 15.0 Hz), 4.14 (2H, t, J=6.6 Hz), 6.80 (2H, d, J=8.4 Hz), 7.05 (2H, d, J=8.4 Hz), 7.46 (3H, m), 7.88 (3H, m), 12.40 (1H, brs).

EXAMPLE 33

Ethyl 2-acetylamino-3-(4-[2-(5-methyl-2-phenyl-4-oxazolyl)ethoxy]phenyl]propionate Sodium hydride (60% in oil, 440 mg, 11.0 mmol) was washed twice with n-hexane (5 ml) under a nitrogen atmosphere, and suspended in N,N-dimethylformamide (50 ml) and ice-cooled. To this suspension was added ethyl N-acetyl-L-tyrosine ester (2.51 g, 10.0 mmol) over 15 min. Ten minutes later when hydrogen bubbling ended, a solution of 2-(5-methyl-2-phenyl-4-oxazolyl)ethyl p-toluenesulfonate (3.57 g, 10.0 mmol) in N,N-dimethylformamide (50 ml) was added. The mixture was stirred at 80° C. for 3 hr, and water (50 ml) and ethyl acetate (100 ml×2) were added for partition. The obtained organic layer was washed with saturated brine (100 ml), dried over magnesium sulfate and concentrated under reduced pressure. The obtained residue was purified by silica gel column chromatography (developing solvent; dichloromethane:methanol=98:2) to give the title compound (1.63 g, yield 37%) as a white solid.

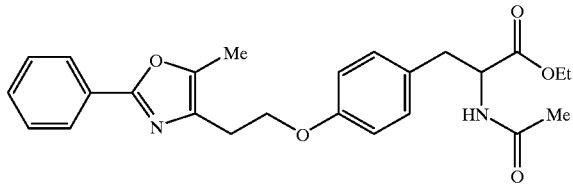

$^1$H-NMR (CDCl$_3$) δ ppm, 300 MHz: 1.25 (3H, t, J=7.1 Hz), 1.97 (3H, s), 2.37 (3H, s), 2.97 (2H, t, J=6.7 Hz), 3.05 (2H, m), 4.16 (2H, q, J=7.1 Hz), 4.21 (2H, t, J=6.7 Hz), 4.81 (1H, m), 5.86 (1H, brd, J=7.8 Hz), 6.82 (2H, d, J=8.7 Hz), 7.43 (3H, m), 7.97 (2H, m).

EXAMPLE 34

2-Acetylamino-3-[4-[2-(5-methyl-2-phenyl-4-oxazolyl)ethoxy]phenyl]propionamide

Ethyl 2-acetylamino-3-[4-[2-(5-methyl-2-phenyl-4-oxazolyl)ethoxy]phenyl]propionate (1.63 g, 3.73 mmol) obtained in Example 33 was dissolved in methanol-tetrahydrofuran (1:1, 50 ml). 28% Aqueous ammonia (20 ml) was added and the mixture was stirred at room temperature for 2 days. Thereto was added 1N aqueous sodium hydroxide solution (30 ml) and the mixture was stirred for 1 hr. The solvent was evaporated under reduced pressure and the obtained residue was partitioned between tetrahydrofuran-ethyl acetate (1:1, 100 ml) and water (50 ml). The organic layer was washed with saturated brine (50 ml), dried over magnesium sulfate and concentrated under reduced pressure. The residue (1.00 g) was washed with hot methanol to give the title compound (560 mg, yield 36%) as a white solid.

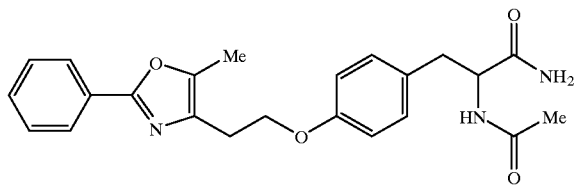

mp: 223.9–225.7° C.;

$^1$H-NMR (DMSO-$d_6$) δ ppm, 300 MHz: 1.73 (3H, s), 2.34 (3H, s), 2.63 (1H, dd, J=8.4 and 12.9 Hz), 2.89 (3H, m), 4.15 (2H, t, J=6.6 Hz), 4.32 (1H, m), 6.81 (2H, d, J=8.4 Hz), 6.97 (1H, brs), 7.12 (2H, d, J=8.4 Hz), 7.37 (1H, brs), 7.48 (3H, m), 7.80–8.00 (3H, m).

EXAMPLE 35

Methyl 2-hydroxy-3-[4-[2-(5-methyl-2-phenyl-4-oxazolyl)ethoxy]phenyl]propionate

Sodium hydride (60% in oil, 247 mg, 6.17 mmol) was washed twice with n-hexane (5 ml) under a nitrogen atmosphere, suspended in N,N-dimethylformamide (50 ml) and ice-cooled. To this suspension was added methyl 3-(4-hydroxyphenyl)lactate (1.10 g, 5.61 mmol) over 15 min. Ten minutes later when hydrogen bubbling ended, a solution of ethyl 2-(5-methyl-2-phenyl-4-oxalyl)methanesulfonate (1.74 g, 3.17 mol) in N,N-dimethylformamide (50 ml) was added. The mixture was stirred at 80° C. for 3 hr, and water (100 ml) and ethyl acetate (100 ml×2) were added for partition. The obtained organic layer was washed with saturated brine (100 ml), dried over magnesium sulfate and concentrated under reduced pressure. The obtained residue was purified by silica gel column chromatography (developing solvent; n-hexane:ethyl acetate=7:3) to give the title compound (754 mg, yield 35%) as a white solid.

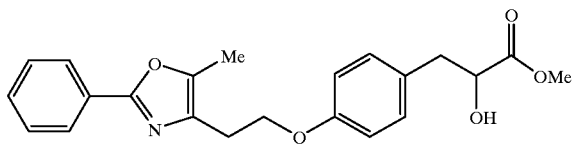

¹H-NMR (CDCl₃) δ ppm, 300 MHz: 2.36 (3H, s), 2.66 (1H, d, J=6.3 Hz), 2.87–3.08 (4H, m), 3.76 (3H, s), 4.21 (2H, d, J=6.7 Hz), 4.41 (1H, m), 6.82 (2H, d, J=8.7 Hz), 7.09 (2H, d, J=8.7 Hz), 7.42 (3H, m), 7.97 (2H, m).

EXAMPLE 36

2-Hydroxy-3-(4-[2-(5-methyl-2-phenyl-4-oxazolyl)ethoxy]phenyl]propionamide

Methyl 2-hydroxy-3-[4-[2-(5-methyl-2-phenyl-4-oxazolyl)ethoxy]phenyl]propionate (754 mg, 1.98 mmol) obtained in Example 35 was dissolved in methanol-tetrahydrofuran (1:1, 6 ml). 28% Aqueous ammonia (3 ml) was added and the mixture was stirred at room temperature for 2 days. Thereto was added 1N aqueous sodium hydroxide solution (1 ml) and the mixture was stirred for 1 hr. The reaction mixture was partitioned between tetrahydrofuran-ethyl acetate (1:1, 30 ml) and water (10 ml). The organic layer was washed with saturated brine (10 ml), dried over magnesium sulfate and concentrated under reduced pressure to give the title compound (700 mg, yield 96%) as a white solid.

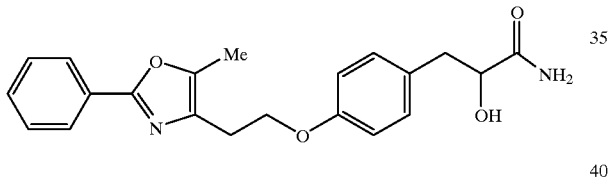

¹H-NMR (DMSO-d₆) δ ppm, 300 MHz: 2.35 (3H, s), 2.61 (1H, dd, J=8.1 and 13.8 Hz), 2.86 (1H, dd, J=3.6 and 13.8 Hz), 2.90 (2H, t, J=6.6 Hz), 3.92 (1H, m), 4.16 (2H, t, J=6.6 Hz), 5.31 (1H, d, J=6.0 Hz), 6.82 (2H, d, J=8.7 Hz), 7.06–7.13 (4H, m), 7.48 (3H, m), 7.89 (2H, m).

EXAMPLE 37

2-Methoxycarbonyloxy-3-[4-[2-(5-methyl-2-phenyl-4-oxazolyl)ethoxy]phenyl]propionamide To a solution of 2-hydroxy-3-[4-[2-(5-methyl-2-phenyl-4-oxazolyl)ethoxy]phenyl]propionamide (550 mg, 1.50 mmol) obtained in Example 36 in dichloromethane-tetrahydrofuran (1:1, 50 ml) was added equivalent of methyl chloroformate and triethylamine under ice-cooling until the reaction completed. The mixture was stirred for 1 hr, and the reaction mixture was diluted with ethyl acetate (100 ml) and washed successively with saturated brine, 1N hydrochloric acid, saturated aqueous sodium hydrogencarbonate solution and saturated brine. The mixture was dried over magnesium sulfate and concentrated under reduced pressure. The obtained residue was purified by silica gel column chromatography (developing solvent; dichloromethane:methanol= 98:2) to give the title compound (110 mg, yield 17%) as a white solid.

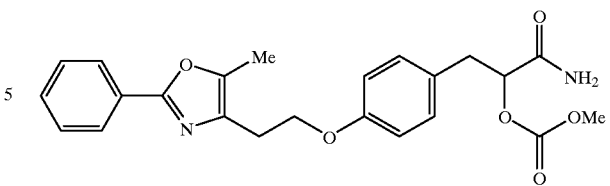

mp: 171.3–173.6° C.;
¹H-NMR (CDCl₃) δ ppm 300 MHz: 2.37 (3H, s), 2.96 (2H, t, J=6.6 Hz), 3.09 (1H, dd, J=6.6 and 14.5 Hz), 3.20 (1H, dd, J=4.2 and 14.5 Hz), 3.76 (3H, s), 4.21 (2H, t, J=6.6 Hz), 5.22 (1H, dd, J=4.2 and 6.6 Hz), 5.36 (1H, brs), 5.91 (1H, brs), 6.83 (2H, d, J=8.4 Hz), 7.11 (2H, d, J=8.4 Hz), 7.41 (3H, m), 7.97 (2H, m).

EXAMPLE 38

Diphenyl 2-[4-[2-(5-methyl-2-phenyl-4-oxazolyl)ethoxy]benzyl]malonate

The title compound was obtained according to the method described in WO95/18125.

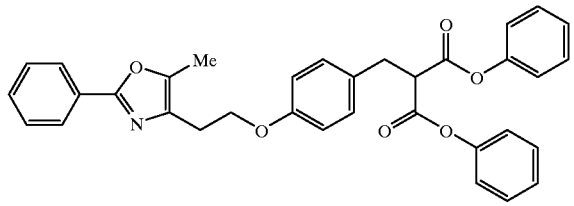

EXAMPLE 39

Dibenzyl 2-[4-[2-(5-methyl-2-phenyl-4-oxazolyl)ethoxy]benzyl]malonate

The title compound was obtained according to the method described in WO95/18125.

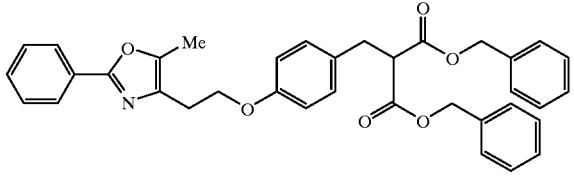

¹H-NMR (CDCl₃) δ ppm, 300 MHz: 2.38 (3H, s), 2.98 (2H, t, J=6.7 Hz), 3.20 (2H, d, J=7.9 Hz), 3.74 (1H, t, J=8.6 Hz), 4.22 (2H, t, J=6.7 Hz), 5.11 (4H, s), 6.78 (2H, d, J=8.7 Hz), 7.06 (2H, d, J=8.7 Hz), 7.15–7.35 (10H, m), 7.42 (3H, m), 8.01 (2H, m).

EXAMPLE 40 tert-Butyl methyl 2-[4-[2-(5-methyl-2-phenyl-4-oxazolyl)ethoxy]benzylidene]malonate To a solution of [(5-methyl-2-phenyloxazol-4-yl)ethoxy]benzaldehyde (4.0 g, 13.1 mmol) in toluene were added acetic acid (0.41 ml, 6.5 mmol), piperidine (0.64 ml, 6.5 mmol) and tert-butyl methyl malonate (2.8 ml, 15.6 mmol). While removing water through Dean-Stark trap, the mixture was refluxed under heating for 1.5 hr. After completion of the reaction, toluene (30 ml) was added and the mixture was washed with water (20 ml×3) and saturated brine (50 ml), dried over magnesium sulfate and concentrated under reduced pressure. The crude product was purified by silica gel column chromatography (developing solvent; n-hexane:ethyl acetate=75:25) to give the title compound (5.4 g, yield 89%, 1:1 geometric isomer mixture) as a pale yellow oil.

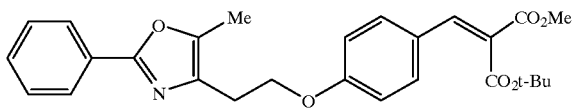

$^1$H-NMR (CDCl$_3$) δ ppm, 300 MHz: 1.52, 1.54 (9H, 2s), 2.37 (3H, s), 2.99 (2H, t, J=6.7 Hz), 3.82, 3.83 (3H, 2s), 4.27, 4.28 (2H, 2t, J=6.7 Hz), 6.88 (2H, 2d, J=8.8 Hz), 7.34–7.48 (5H, m), 7.56, 7.57 (1H, 2s), 7.98 (2H, m).

EXAMPLE 41 tert-Butyl methyl 2-[4-[2-(5-methyl-2-phenyl-4-oxazolyl)ethoxy]benzyl]malonate

To a suspension of 10% palladium carbon (1.1 g) in tetrahydrofuran (4.0 ml) was added a mixed solution of tert-butyl methyl 2-[4-[2-(5-methyl-2-phenyl-4-oxazolyl)ethoxy]benzylidene]malonate in methanoltetrahydrofuran (2:1, 36.0 ml), and the mixture was stirred at room temperature for 14 hr under hydrogen pressurization (3 atm). After completion of the reaction, the palladium carbon catalyst was filtered through celite and the filtrate was concentrated under reduced pressure to give the title compound (5.4 g, quant) as a yellow oil.

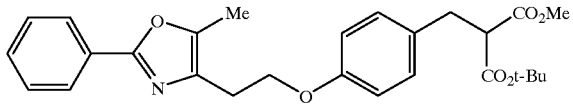

$^1$H-NMR (CDCl$_3$) δ ppm, 300 MHz: 1.39 (9H, s), 2.38 (3H, s), 3.00 (2H, m), 3.10 (2H, d, J=7.8 Hz), 3.51 (1H, t, J=7.8 Hz), 3.68 (3H, s), 4.23 (2H, m), 6.80 (2H, d, J=8.3 Hz), 7.09 (2H, d, J=8.3 Hz), 7.42 (3H, m), 8.01 (2H, m).

EXAMPLE 42

2-tert-Butyloxycarbonyl 3-[4-[2-(5-methyl-2-phenyl-4-oxazolyl)ethoxy]phenyl]propionate To a solution of tert-butyl methyl 2-[4-[2-(5-methyl-2-phenyl-4-oxazolyl)ethoxy]benzyl]malonate (5.4 g, 11.5 mmol) obtained in Example 41 in methanol (30.0 ml) was added 1N aqueous sodium hydroxide solution (13 ml, 12.7 mmol), and the mixture was stirred at room temperature for 24 hr. 1N Hydrochloric acid and water were added to the reaction mixture at 0° C. and the mixture was extracted with chloroform (20 ml×3). The organic layer was washed with water (50 ml) and saturated brine (50 ml), dried over magnesium sulfate and concentrated under reduced pressure. The crude product was purified by silica gel column chromatography (developing solvent; n-hexane:ethyl acetate=8:2→chloroform:methanol=9:1) to give the title compound (4.5 g, yield 87%) as colorless amorphous.

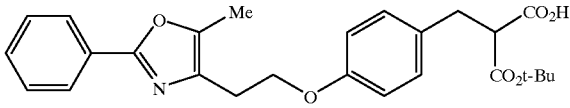

$^1$H-NMR (CDCl$_3$) δ ppm 300 MHz: 1.40 (9H, s), 2.36 (3H, m), 2.96 (2H, t, J=6.6 Hz), 3.14 (2H, d, J=7.4 Hz), 3.56 (1H, t, J=7.4 Hz), 4.16 (2H, t, J=6.6 Hz), 6.79 (2H, d, J=8.4 Hz), 7.11 (2H, d, J=8.4 Hz), 7.42 (3H, m), 7.96 (2H, m).

EXAMPLE 43

Benzyl tert-butyl 2-[4-[2-(5-methyl-2-phenyl-4-oxazolyl)ethoxy]benzyl]malonate

To a solution of 2-tert-butyloxycarbonyl 3-[4-[2-(5-methyl-2-phenyl-4-oxazolyl)ethoxy]phenyl]propionate (1.0 g, 2.2 mmol) obtained in Example 42 in dimethylformamide (8 ml) were added sodium hydrogencarbonate (744 mg, 8.9 mmol) and benzyl bromide (0.29 ml, 2.4 mmol), and the mixture was stirred at room temperature for 3 days. To the reaction mixture was added ethyl acetate (50 ml) and the mixture was washed with water (15 ml×3) and saturated brine (20 ml), dried over sodium sulfate and concentrated under reduced pressure. The crude product was purified by silica gel column chromatography (developing solvent; n-hexane:ethyl acetate=8:2) to give the title compound (1.1 g, yield 93%) as colorless crystals.

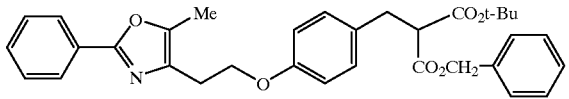

$^1$H-NMR (CDCl$_3$) δ ppm, 300 MHz: 1.33 (9H, s), 2.37 (3H, s), 2.96 (2H, t, J=6.7 Hz), 3.11 (2H, d, J=7.9 Hz), 3.56 (1H, t, J=7.9 Hz), 4.21 (2H, t, J=6.7 Hz), 5.07 (1H, d, J=12.3 Hz), 5.14 (1H, d, J=12.3 Hz), 6.78 (2H, d, J=8.6 Hz), 7.07 (2H, d, J=8.6 Hz), 7.26–7.32 (5H, m), 7.41 (3H, m), 7.97 (2H, m).

EXAMPLE 44

2-Benzyloxycarbonyl 3-[4-[2-(5-methyl-2-phenyl-4-oxazolyl)ethoxy]phenyl]propionate To a solution of tert-butyl 2-[4-[2-(5-methyl-2-phenyl-4-oxazolyl)ethoxy]benzyl]malonate (2.5 g, 4.7 mmol) obtained in Example 43 in chloroform (30 ml) was added trifluoroacetic acid (21.5 ml, 0.28 mmol) at 0° C., and the mixture was stirred at room temperature for 2.5 hr. The reaction mixture was concentrated under reduced pressure and chloroform (150 ml) was added. The mixture was washed with water (30 ml×4) and saturated brine (30 ml), dried over magnesium sulfate and concentrated under reduced pressure. The crude product was purified by silica gel column chromatography (developing solvent; n-hexane:ethyl acetate=8:2→chloroform:methanol=9:1) to give the title compound (2.1 g, yield 92%) as colorless amorphous.

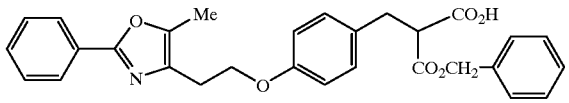

¹H-NMR (CDCl₃) δ ppm, 300 MHz: 2.32 (3H, s), 2.92 (2H, t, J=6.5 Hz), 3.15 (2H, d, J=7.7 Hz), 3.67 (1H, t, J=7.7 Hz), 4.09 (2H, t, J=6.5 Hz), 5.09 (2H, s), 6.72 (2H, d, J=8.6 Hz), 7.03 (2H, d, J=8.6 Hz), 7.19–7.25 (5H, m), 7.36 (3H, m), 7.91 (2H, m).

EXAMPLE 45

Isopropyl 4-nitrobenzyl 2-[4-[2-(5-methyl-2-phenyl-4-oxazolyl)ethoxy]benzylidene]malonate (Step 1)

4-Nitrobenzyl isopropyl malonate

1N Hydrochloric acid (200 ml) and ethyl acetate (200 ml) were added to 4-nitrobenzyl malonate magnesium salt (28 g, 56 mmol). The organic layer was partitioned, washed with saturated brine (50 ml×2), and dried over magnesium sulfate. Ethyl acetate was evaporated to give a white solid (23.2 g, yield 87%).

The obtained solid (13 g, 55 mmol) was suspended in dichloromethane (100 ml). Dimethylformamide (1 ml) was added and oxalyl chloride (8.9 g) was gradually added under ice-cooling. The mixture was stirred at room temperature for 1.5 hr and the solvent was evaporated under reduced pressure to give a yellow oil (15.5 g).

The obtained oil (7.8 g, 27.3 mmol) was dissolved in dichloromethane (100 ml), and isopropyl alcohol (100 ml) and then triethylamine (7.6 ml, 54.6 mmol) were added under ice-cooling, which was followed by stirring for 1 hr.

The solvent was evaporated under reduced pressure, and ethyl acetate (100 ml) and saturated brine (100 ml) were added. The organic layer was partitioned, washed with saturated brine (50 ml), and dried over magnesium sulfate. Ethyl acetate was evaporated under reduced pressure. The obtained brown oil was purified by silica gel column chromatography (developing solvent; hexane:ethyl acetate=75:25) and the fraction containing the objective substance was concentrated under reduced pressure to give the title compound (6.62 g, yield 86%) as a yellow oil.

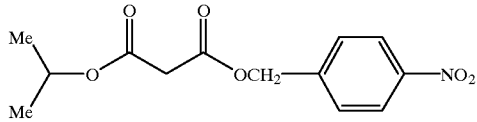

¹H-NMR (CDCl₃) δ ppm, 300 MHz: 1.25 (6H, d, J=6.0 Hz), 3.44 (2H, s), 5.01–5.11 (1H, m), 5.28 (2H, s), 7.54 (2H, d, J=8.7 Hz), 8.23 (2H, d, J=8.7 Hz).

(Step 2)

Isopropyl 4-nitrobenzyl 2-[4-[2-(5-methyl-2-phenyl-4-oxazolyl)ethoxy]benzylidene]malonate To a solution of 4-[2-(5-methyl-2-phenyl-4-oxazolyl)ethoxy]benzaldehyde (3.59 g, 11.7 mmol) synthesized according to the method described in WO95/18125 in toluene (40 ml) were added 4-nitrobenzyl isopropyl malonate (4 g, 14 mmol) obtained in Step 1, acetic acid (351 mg) and piperidine (498 mg). While removing water through Dean-Stark trap, the mixture was refluxed under heating. Two hours later, toluene was evaporated under reduced pressure. The obtained residue was purified by silica gel column chromatography (developing solvent; hexane:ethyl acetate= 65:35) and the fraction containing the objective substance was concentrated under reduced pressure to give the title compound (5.24 g, yield 66%) as a yellow oil.

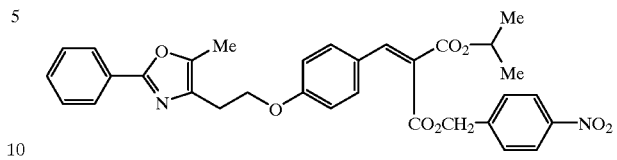

¹H-NMR (CDCl₃) δ ppm, 300 MHz: 1.20–1.30 (6H, m), 2.37 (3H, s), 2.99 (2H, t, J=6.8 Hz), 4.21–4.30 (2H, m), 5.11–5.29 (1H, m), 5.37 (2H, d, J=5.7 Hz), 6.79–6.92 (2H, m), 7.28–7.57 (7H, m), 7.70 (1H, s), 7.93–8.00 (2H, m), 8.18–8.26 (2H, m).

EXAMPLE 46

2-Isopropoxycarbonyl 3-[4-[2-(5-methyl-2-phenyl-4-oxazolyl)ethoxy]phenyl]propionic acid Isopropyl 4-nitrobenzyl 2-[4-[2-(5-methyl-2-phenyl-4-oxazolyl)ethoxy]benzylidene]malonate (5 g, 8.77 mmol) obtained in Example 45 was dissolved in a mixed solvent of methanol-tetrahydrofuran (40 ml–15 ml) and 5% palladium carbon (1 g) was added, which was followed by hydrogenation at room temperature under pressurization (3 kgf/cm²).

Four hours later, the catalyst was filtered through celite and the filtrate was concentrated under reduced pressure. The residue was eluted by silica gel column chromatography (developing solvent; hexane: ethyl acetate=9:1 mixed solvent) and the fraction containing the objective substance was concentrated under reduced pressure to give a crude purified product (600 mg) as a yellow oil. Thereto was added isopropyl ether (2 ml) and the precipitated crystals were collected by filtration and dried to give the title compound (469 mg, yield 12%) as white crystals.

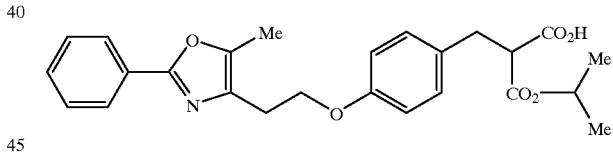

¹H-NMR (CDCl₃) δ ppm, 300 MHz: 1.16 (3H, d, J=6.3 Hz), 1.21 (3H, d, J=6.3 Hz), 2.36 (3H, s), 2.96 (2H, t, J=6.6 Hz), 3.17 (2H, d, J=7.8 Hz), 3.61 (1H, t, J=7.5 Hz), 4.16 (2H, t, J=6.6 Hz), 4.95–5.15 (1H, m), 6.79 (2H, d, J=8.7 Hz), 7.11 (2H, d, J=8.7 Hz), 7.35–7.47 (3H, m), 7.94–8.01 (2H, m).

EXAMPLE 47

Benzyl phenyl 2-[4-[2-(5-methyl-2-phenyl-4-oxazolyl)ethoxy]benzyl]malonate

2-Benzyloxycarbonyl 3-[4-[2-(5-methyl-2-phenyl-4-oxazolyl)ethoxy]phenyl]propionate (1 g, 2.06 mmol) obtained in Example 44, phenol (194 mg, 2.06 mmol), water soluble carbodiimide hydrochloride (474 mg, 2.47 mmol), dimethylaminopyridine (52 mg) and molecular sieves 4A powder (1 g) were added to dichloromethane (12 ml) at room temperature. The mixture was stirred at room temperature for 10 hr, and concentrated under reduced pressure. The obtained residue was purified by silica gel column chromatography (developing solvent; hexane:ethyl acetate= 75:25) and the fraction containing the objective substance was concentrated under reduced pressure to give the title compound (1.1 g, yield 95%) as a colorless oil.

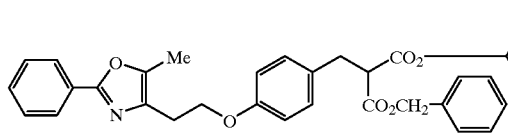

$^1$H-NMR (CDCl$_3$) δ ppm, 300 MHz: 2.37 (3H, s), 2.97 (2H, t, J=6.6 Hz), 3.28 (2H, d, J=7.8 Hz), 3.89 (1H, t, J=8.0 Hz), 4.22 (2H, t, J=6.6 Hz), 5.19 (2H, s), 6.80–6.89 (4H, m), 7.10–7.45 (13H, m), 7.92–8.00 (2H, m).

EXAMPLE 48

2-Phenoxycarbonyl-[4-[2-(5-methyl-2-phenyl-4-oxazolyl)ethoxy]phenyl]propionic acid Benzyl phenyl 2-[4-[2-(5-methyl-2-phenyl-4-oxazolyl)ethoxy]benzyl]malonate (1 g, 1.9 mmol) obtained in Example 47 was added to ethyl acetate (10 ml). 5% Palladium carbon (100 mg) was added and catalytic hydrogenation was performed at room temperature and under atmospheric pressure.

Seven hours later, the catalyst was filtered through celite and the solvent was evaporated under reduced pressure. To the residue was added diethyl ether (4 ml) and the precipitated crystals were collected by filtration and dried to give the title compound (680 mg, yield 74%) as white crystals.

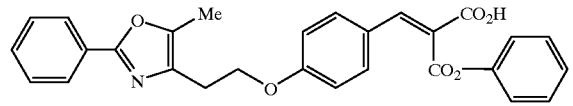

mp: 144.4–145.8° C.;

$^1$H-NMR (CDCl$_3$) δ ppm, 300 MHz: 2.36 (3H, s), 2.98 (2H, t, J=6.5 Hz), 3.29 (2H, d, J=7.5 Hz), 3.88 (1H, t, J=7.7 Hz), 4.16 (2H, t, J=6.6 Hz), 6.82 (2H, d, J=8.4 Hz), 6.97 (2H, d, J=7.2 Hz), 7.16–7.42 (8H, m), 7.94–8.00 (2H, m).

EXAMPLE 49

Diisopropyl 2-[4-[2-(5-methyl-2-phenyl-4-oxazolyl)ethoxy]benzylidene]malonate

To a solution of 4-[2-(5-methyl-2-phenyl-4-oxazolyl)ethoxy]benzaldehyde (3.07 g, 10 mmol) synthesized according to the method described in WO95/18125 in toluene (40 ml) were added diisopropyl malonate (1.88 g, 10 mmol), acetic acid (300 mg) and piperidine (425 mg). While removing water through Dean-Stark trap, the mixture was refluxed under heating. Eight hours later, toluene was evaporated under reduced pressure. The obtained residue was purified by silica gel column chromatography (developing solvent; hexane:ethyl acetate=75:25) and the fraction containing the objective substance was concentrated under reduced pressure to give the title compound (4.2 g, yield 88%) as a yellow oil.

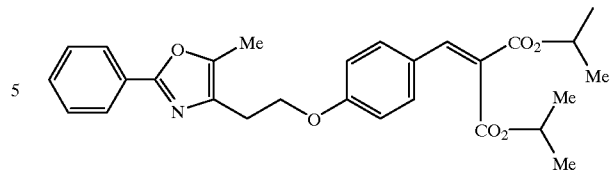

$^1$H-NMR (CDCl$_3$) δ ppm, 300 MHz: 1.29 (6H, d, J=6.0 Hz), 1.30 (6H, d, J=6.0 Hz), 2.37 (3H, s), 2.98 (2H, t, J=6.8 Hz), 4.28 (2H, t, J=6.6 Hz), 5.08–5.30 (2H, m), 6.88 (2H, d, J=8.7 Hz), 7.35–7.46 (5H, m), 7.60 (1H, s), 7.93–8.00 (2H, m).

EXAMPLE 50

Diisopropyl 2-[4-[2-(5-methyl-2-phenyl-4-oxazolyl)ethoxy]benzyl]malonate

Diisopropyl 2-[4-[2-(5-methyl-2-phenyl-4-oxazolyl)ethoxy]benzylidene]malonate (4 g, 8.4 mmol) obtained in Example 49 was dissolved in methanol (30 ml). 5% Palladium carbon (400 mg) was added and catalytic hydrogenation was performed at room temperature and under pressurization (3 kgf/cm$^2$).

Eight hours later, the catalyst was filtered through celite and the filtrate was concentrated under reduced pressure. The residue was purified by silica gel column chromatography (developing solvent; hexane:ethyl acetate=8:2) and the fraction containing the objective substance was concentrated under reduced pressure to give the title compound (4 g, yield 99%) as a pale-yellow oil.

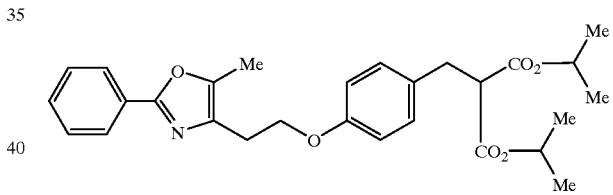

$^1$H-NMR (CDCl$_3$) δ ppm, 300 MHz: 1.16 (6H, d, J=6.0 Hz), 1.20 (6H, d, J=6.0 Hz), 2.36 (3H, s), 2.96 (2H, t, J=6.6 Hz), 3.11 (2H, d, J=8.1 Hz), 3.52 (1H, t, J=7.7 Hz), 4.20 (2H, t, J=6.6 Hz), 4.93–5.05 (2H, m), 6.80 (2H, d, J=8.7 Hz), 7.10 (2H, d, J=8.4 Hz), 7.35–7.48 (3H, m), 7.93–8.01 (2H, m).

EXAMPLE 51

3-[4-[2-(5-Methyl-2-phenyl-4-oxazolyl)ethoxy]benzylidene]pentane-2,4-dione

To a solution of 4-[2-(5-methyl-2-phenyl-4-oxazolyl)ethoxy]benzaldehyde (3.07 g, 10 mmol) synthesized according to the method described in WO95/18125 in toluene (40 ml) were added 2,4-pentanedione (1.2 g, 12 mmol), acetic acid (300 mg) and piperidine (425 mg). While removing water through Dean-Stark trap, the mixture was refluxed under heating. Five hours later, toluene was evaporated under reduced pressure, and the obtained residue was purified by silica gel column chromatography (developing solvent; hexane:ethyl acetate=1:1) and the fraction containing the objective substance was concentrated under reduced pressure to give the title compound (2.3 g, yield 60%) as a yellow oil.

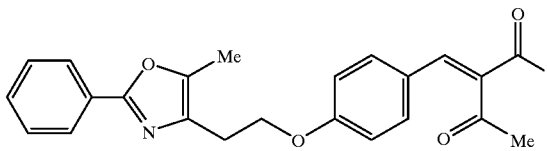

EXAMPLE 52

3-[4-[2-(5-Methyl-2-phenyl-4-oxazolyl)ethoxy]benzyl]pentane-2,4-dione

3-[4-[2-(5-Methyl-2-phenyl-4-oxazolyl)ethoxy]benzylidene]pentane-2,4-dione (2 g, 5.1 mmol) obtained in Example 51 was dissolved in methanol (30 ml). 5% Palladium carbon (400 mg) was added and catalytic hydrogenation was performed at room temperature and under pressurization (3 kgf/cm$^2$).

Five hours later, the catalyst was filtered through celite and the filtrate was concentrated under reduced pressure. The residue was purified by silica gel column chromatography (developing solvent; hexane:ethyl acetate=3:2) and the fraction containing the objective substance was concentrated under reduced pressure to give the title compound (1.74 g, yield 87%) as a pale-yellow oily keto-enol tautomer (keto compound:enol compound=37:63).

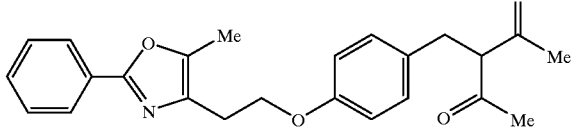

$^1$H-NMR (CDCl$_3$) δ ppm, 300 MHz: 2.06 (3.78H, s), 2.11 (2.22H, s), 2.37 (3H, s), 2.92–3.03 (2H, m), 3.08 (0.74H, d, J=7.8 Hz), 3.57 (1.26H, s), 3.95 (0.37H, t, J=7.5 Hz), 4.18–4.26 (2H, m), 6.78–6.94 (2H, m), 6.99–7.08 (2H, m), 7.37–7.50 (3H, m), 7.93–8.01 (2H, m).

EXAMPLE 53

3-Methyl-3-[4-[2-(5-methyl-2-phenyl-4-oxazolyl)ethoxy]benzyl]pentanone-2,4-dione 3-[4-[2-(5-Methyl-2-phenyl-4-oxazolyl)ethoxy]benzyl]pentane-2,4-dione (750 mg, 1.92 mmol) obtained in Example 52 was dissolved in acetone (20 ml) and potassium carbonate (800 mg) and methyl iodide (5 ml) were added at room temperature, which was followed by refluxing under heating.

Eight hours later, insoluble matter was filtered off and the filtrate was concentrated under reduced pressure. The residue was purified by silica gel column chromatography (developing solvent; hexane:ethyl acetate=7:3) and the fraction containing the objective substance was concentrated under reduced pressure to give the title compound (670 mg, yield 86%) as a pale-yellow oil.

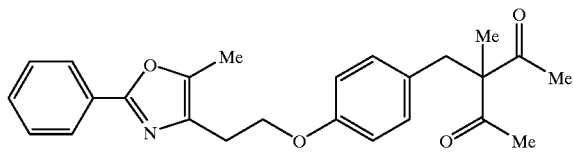

$^1$H-NMR (CDCl$_3$) δ ppm, 300 MHz: 1.27 (3H, s), 2.09 (6H, s), 2.36 (3H, s), 2.96 (2H, t, J=6.6 Hz), 3.10 (2H, s), 4.20 (2H, t, J=6.6 Hz), 6.78 (2H, d, J=8.4 Hz), 6.96 (2H, d, J=8.4 Hz), 7.38–7.44 (3H, m), 7.94–8.00 (2H, m).

EXAMPLE 54

Diethyl 4-[2-(5-methyl-2-phenyl-4-oxazolyl)ethoxy]benzylidenemalonate

4-[2-(5-Methyl-2-phenyl-4-oxazolyl)ethoxy]benzaldehyde (8.0 g, 26.0 mmol) synthesized according to the method described in WO95/18125, diethyl malonate (4.79 g, 29.9 mmol), acetic acid (1.04 ml) and piperidine (1.03 ml) were mixed. While removing water through Dean-Stark trap, the mixture was refluxed under heating. Three and a half hours later, toluene was evaporated and the obtained residue was recrystallized from ethyl acetate-hexane to give the title compound (9.55 g, yield 82%) as pale-brown white crystals.

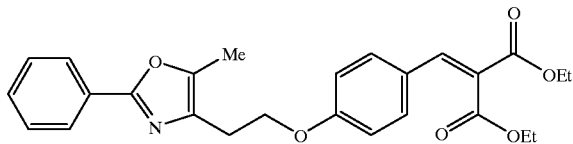

$^1$H-NMR (CDCl$_3$) δ ppm, 300 MHz: 1.31 (6H, m), 2.37 (3H, s), 2.98 (2H, t, J=6.6 Hz), 4.19–4.39 (6H, m), 6.88 (2H, d, J=8.7 Hz), 7.32–7.50 (5H, m), 7.65 (1H, s), 7.97 (2H, m).

EXAMPLE 55

Diethyl 4-[2-(5-methyl-2-phenyl-4-oxazolyl)ethoxy]benzylmalonate

Diethyl 4-[2-(5-methyl-2-phenyl-4-oxazolyl)ethoxy]benzylidenemalonate (9.55 g, 21.3 mmol) obtained in Example 54 was dissolved in methanol (48 ml) and tetrahydrofuran (32 ml). 5% Palladium carbon (1 g) was added and the mixture was vigorously stirred at normal temperature under a hydrogen atmosphere (3.1 kgf/cm$^2$). One and a half hours later, the catalyst was filtered off. The solvent was evaporated to give a crude solid. Recrystallization from ethyl acetate-hexane gave the title compound (5.23 g, yield 55%) as white crystals.

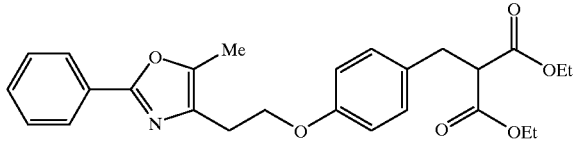

mp: 69.8–70.5° C.

$^1$H-NMR (CDCl$_3$) δ ppm, 300 MHz: 1.27 (6H, t, J=7.1 Hz), 2.43 (3H, s), 3.02 (2H, t, J=6.7 Hz), 3.20 (2H, d, J=7.8 Hz), 3.64 (1H, t, J=7.8 Hz), 4.20 (2H, q, J=7.1 Hz), 4.21 (2H, q, J=7.1 Hz), 4.27 (2H, t, J=6.8 Hz), 6.87 (2H, d, J=8.6 Hz), 7.16 (2H, d, J=8.6 Hz), 7.47 (3H, m), 8.04 (2H, m).

EXAMPLE 56

2-Ethoxycarbonyl-3-[4-[2-(5-methyl-2-phenyl-4-oxazolyl)ethoxy]phenyl]propionic acid Diethyl 4-[2-(5-methyl-2-phenyl-4-oxazolyl)ethoxy] benzylmalonate (4.60 g, 10.2 mmol) obtained in Example 55 was dissolved in a mixed solvent of ethanol (50 ml) and tetrahydrofuran (25 ml), and the mixture was stirred at room temperature for 18 hr. The solvent was evaporated to give a crude solid. Water (20 ml) and 1N sodium hydroxide (30 ml) were added to dissolve said crude solid. 1N Hydrochloric acid was added at 0° C., and the mixture was extracted three times with ethyl acetate (30 ml). The extracted organic layer was washed with brine, dried over sodium sulfate and concentrated to dryness to give a crude title compound (4.7 g), which was purified and concentrated by silica gel column chromatography (developing solvent; chloroform:methanol=100:1→50:1) to give the title compound. This compound was dissolved in 1N sodium hydroxide (10 ml) and washed twice with ethyl acetate (30 ml). 1N Hydrochloric acid (15 ml) was added to the aqueous layer, and the mixture was extracted three times with ethyl acetate (30 ml). The extracted organic layer was washed with brine, dried over sodium sulfate and concentrated to dryness to give the title compound (2.91 g, yield 67%) as white crystals.

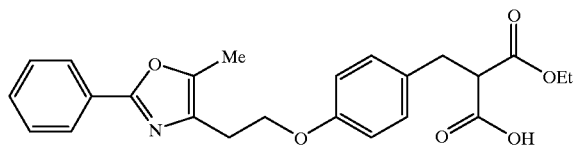

mp: 95.1–96.0° C.; $^1$H-NMR (CDCl$_3$) δ ppm, 300 MHz: 1.15 (6H, t, J=7.1 Hz), 2.30 (3H, s), 2.90 (2H, t, J=6.6 Hz), 3.12 (2H, d, J=7.6 Hz), 3.58 (1H, t, J=7.6 Hz), 4.07–4.14 (4H, m), 6.74 (2H, d, J=8.6 Hz), 7.05 (2H, d, J=8.6 Hz), 7.36 (3H, m), 7.90 (2H, m).

EXAMPLE 57

Dimethyl 4-[2-(5-ethyl-2-pyridyl)ethoxy] benzylidene]malonate

5-[4-[2-(5-Ethyl-2-pyridyl)]ethoxy]benzaldehyde (8.0 g, 31.4 mmol) synthesized according to the method described in Japanese Patent Unexamined Publication No. 63-139182, dimethyl malonate (6.21 g, 47.1 mmol), acetic acid (1.0 ml) and piperidine (1.0 ml) were mixed. While removing water through Dean-Stark trap, the mixture was refluxed under heating. Forty minutes later, toluene was evaporated and the obtained residue was purified and concentrated by silica gel column chromatography (developing solvent; hexane:ethyl acetate=7:3→1:1→1:2) to give the title compound (6.31 g, yield 54%) as a brown oil.

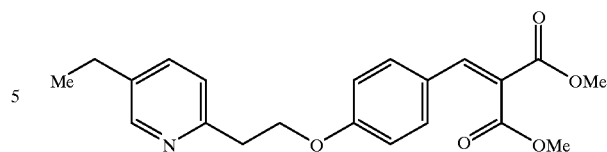

$^1$H-NMR (CDCl$_3$) δ ppm, 300 MHz: 1.26 (3H, t, J=7.6 Hz), 2.64 (2H, q, J=7.6 Hz), 3.23 (2H, t, J=6.8 Hz), 3.83 (3H, s), 3.85 (3H, s), 4.38 (2H, t, J=6.6 Hz), 6.89 (2H, d, J=9.0 Hz), 7.17 (1H, d, J=8.1 Hz), 7.36 (2H, d, J=8.7 Hz), 7.46 (1H, dd, J=2.1 and 8.1 Hz), 7.69 (1H, s), 8.39 (1H, d, J=1.8 Hz).

EXAMPLE 58

Dimethyl 4-[2-(5-ethyl-2-pyridyl)ethoxy]benzyl] malonate

Dimethyl 4-[2-(5-ethyl-2-pyridyl)ethoxy]benzylidene] malonate (6.3 g, 17.1 mmol) obtained in Example 57 was dissolved in methanol (30 ml) and dioxane (30 ml). Palladium hydroxide (1 g) was added, and the mixture was vigorously stirred at normal temperature under a hydrogen atmosphere (3.1 kgf/cm$^2$). Five and a half hours later, the catalyst was filtered off. The solvent was evaporated to give a crude solid, which was purified and concentrated by silica gel column chromatography (developing solvent; hexane:ethyl acetate=7:3) to give the title compound (4.60 g, yield 73%) as a yellow-brown oil.

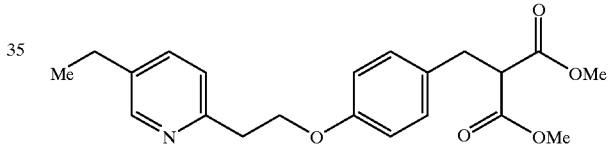

$^1$H-NMR (CDCl$_3$) δ ppm, 300 MHz: 1.24 (3H, t, J=7.6 Hz), 2.63 (2H, q, J=7.5 Hz), 3.14 (2H, d, J=7.5 Hz), 3.21 (2H, t, J=6.6 Hz), 3.61 (1H, t, J=6.8 Hz), 3.69 (6H, s), 4.31 (2H, t, J=6.8 Hz), 6.81 (2H, d, J=9.6 Hz), 7.08 (2H, d, J=8.4 Hz), 7.18 (1H, d, J=8.1 Hz), 7.45 (1H, dd, J=2.1 and 7.8 Hz), 8.39 (1H, d, J=2.1 Hz).

EXAMPLE 59

Dimethyl 2-methyl-2-[4-[2-(5-methyl-2-phenyl-4-oxazolyl)ethoxy]benzyl]malonate

Dimethyl 4-[2-(5-methyl-2-phenyl-4-oxazolyl)ethoxy] benzylmalonate (4.24 g, 10.0 mmol) synthesized according to the method described in WO95/18125 was dissolved in dimethylformamide (40 ml), and sodium hydride (60% in oil, 480 mg, 12.0 mmol) was added at 0° C., which was followed by stirring for 2 hr. Methyl iodide (0.93 ml, 15.0 mmol) was added at room temperature and, 2.5 hours later, 1N sodium hydrogensulfate (100 ml) was added. The mixture was extracted three times with ethyl acetate. The extracted organic layer was washed with brine, dried over sodium sulfate and concentrated to dryness to give a crude title compound, which was purified and concentrated by silica gel column chromatography (developing solvent; hexane:ethyl acetate=10:1→7:1→5:1) to give the title compound (2.71 g, yield 62%) as a white solid.

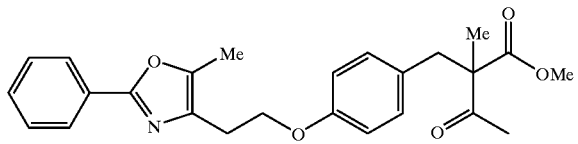

mp: 75.1–76.0° C.;

¹H-NMR (CDCl₃) δ ppm, 300 MHz: 1.32 (3H, s), 2.36 (3H, s), 2.96 (2H, t, J=6.6 Hz), 3.15 (2H, s), 3.71 (6H, s), 4.21 (2H, t, J=6.3 Hz), 6.79 (2H, d, J=6.6 Hz), 6.99 (2H, d, J=6.6 Hz), 7.43 (3H, m), 7.97 (2H, m).

EXAMPLE 60

2-methoxycarbonyl 3-[4-[2-(5-methyl-2-phenyl-4-oxazolyl)ethoxy]phenyl]propionic acid (Step 1)

5-[4-[2-(5-Methyl-2-phenyl-4-oxazolyl)ethoxy]benzilidene]Meldrum's acid

To a solution of 4-[2-(5-methyl-2-phenyl-4-oxazolyl)ethoxy]benzylbenzaldehyde (15.4 g, 50 mmol) synthesized according to the method described in WO95/18125 in toluene (200 ml) were added Meldrum's acid (6.49 g, 45 mmol), acetic acid (1.5 g), piperidine (2.1 g) and molecular sieves 3A powder (10 g). The mixture was stirred at room temperature. Five hours later, molecular sieves 3A powder was filtered off and the filtrate was washed with 10% hydrochloric acid (50 ml) and saturated brine (50 ml×3), dried over magnesium sulfate and concentrated under reduced pressure. Diethyl ether (100 ml) was added to the residue, and the precipitated crystals were collected by filtration and dried to give the title compound (14.4 g, yield 67%) as yellow crystals.

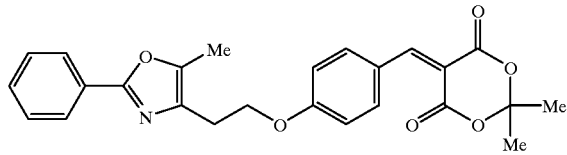

¹H-NMR (CDCl₃) δ ppm, 300 MHz: 1.78 (6H, s), 2.38 (3H, s), 3.02 (2H, t, J=6.8 Hz), 4.37 (2H, t, J=6.5 Hz), 6.98 (2H, d, J=8.7 Hz), 7.35–7.46 (31H, m), 7.94–8.01 (2H, m), 8.21 (2H, d, J=9 Hz), 8.36 (1H, s).

(Step 2)

5-[4-[2-(5-Methyl-2-phenyl-4-oxazolyl)ethoxy]benzyl]-Meldrum's acid

5-[4-[2-(5-Methyl-2-phenyl-4-oxazolyl)ethoxy]benzilidene]-Meldrum's acid (14.4 g, 33 mmol) obtained in Step 1 was dissolved in dioxanemethanol (100 ml–50 ml). 5% Palladium carbon (3 g) was added and catalytic hydrogenation was performed at room temperature and under pressurization (3 kgf/cm²).

Four hours later, the catalyst was filtered through celite and the solvent was evaporated under reduced pressure to give the title compound (14 g, yield 98%) as a white solid.

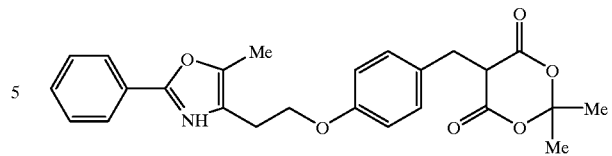

¹H-NMR (CDCl₃) δ ppm, 300 MHz: 1.46 (3H, s), 1.71 (3H, s), 2.36 (3H, s), 2.96 (2H, t, J=6.8 Hz), 3.42 (2H, d, J=4.8 Hz), 3.70 (1H, d, J=5.0 Hz), 4.21 (2H, t, J=6.8 Hz), 6.82 (2H, d, J=8.7 Hz), 7.21 (2H, d, J=8.4 Hz), 7.38–7.46 (3H, m), 7.93–8.00 (2H, m).

(Step 3)

2-methoxycarbonyl 3-[4-[2-(5-methyl-2-phenyl-4-oxazolyl)ethoxy]phenyl]propionic acid 5-[4-[2-(5-Methyl-2-phenyl-4-oxazolyl)ethoxy]benzyl]-Meldrum's acid (14.0 g, 34.2 mmol) obtained in Step 2 was dissolved in methanol (300 ml) and the mixture was refluxed under heating for 17 hr. The reaction mixture was concentrated under reduced pressure to give the title compound (13.1 g) as a white solid.

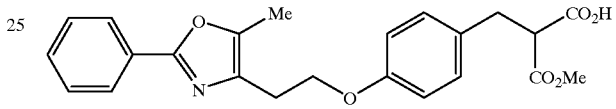

REFERENCE EXAMPLE 1

Dimethyl 2-[4-[2-(5-methyl-2-phenyl-4-oxazolyl)ethoxy]benzyl]malonate

The title compound was obtained according to Example 1' described in WO95/18125.

The insulin sensitivity promoting activity of compound (I') was tested.

EXPERIMENTAL EXAMPLE 1

Evaluation of Insulin Sensitivity Using 3T3-L1 Cells

3T3-L1 cells (purchased from American Type Culture Collection) which were in the n=x+3 passage were purchased and subcultured until the passage number reached n=x+8. The cells were frozen in liquid nitrogen, thawed and subcultured till n=x+11.

0.05% Trypsin-0.53 mM ethylenediaminetetraacetic acid (EDTA) was added and the cells were harvested. The cells were suspended in Dulbecco's modified Eagle's medium (DMEM) [5% fetal bovine serum (FBS), supplemented with 5.6 mM glucose], plated on a 24 well plate at a concentration of 0.5×10⁵ cells/well and cultured. Two days later, the medium was changed to DMEM [5% FBS, supplemented with 5.6 mM glucose] containing 1 μM dexamethasone and 0.5 mM isobutylmethylxanthine and the incubation was continued for 2 more days.

The test compounds were dissolved in dimethyl sulfoxide and diluted 1000-fold with DMEM [2% FBS, supplemented with 5.6 mM glucose] containing insulin (10 ng/ml) to make the final concentration thereof to 0 nM-10 μM, and added to the cells, which cells were incubated for 4 days.

After incubation, isopropanol was added by 200 μl per well and the cells were ruptured by a probe type ultrasonicator. The triglyceride amount was determined using a triglyceride determination kit.

The activity of the compounds was determined by calculating relative triglyceride increase achieved by each compound when that achieved by 10 μM pioglitazone was taken as 100%, and expressed by the dose (EC50) necessary for a 50% increase of triglyceride.

The test compounds were those of Examples 1–3, 5, 8, 15, 16, 18, 19, 22 and 28 and Reference Example 1.

As a control compound, used was a known compound of the following formula. The results are shown in Table 1.
[Control compound]

TABLE 1

| Test compound | EC50 (nM) |
|---|---|
| Example 1 | 0.45 |
| Example 2 | 90.0 |
| Example 3 | 150.0 |
| Example 5 | 7.2 |
| Example 8 | 7.0 |
| Example 15 | 90.0 |
| Example 16 | 53.0 |
| Example 18 | 65.0 |
| Example 19 | 90.0 |
| Example 22 | 90.0 |
| Example 28 | 73.0 |
| Reference Example 1 | 0.38 |
| Control compound | 180.00 |

The above test concerns whether or not the insulin sensitivity of 3T3-L1 cells is promoted. Promotion of insulin sensitivity is said to be an effective treatment of diabetes (non-insulin dependent diabetes mellitus), in which a sufficient release of insulin does not result in lowering of blood glucose level to a normal range.

When insulin acts on 3T3-L1 cells, it not only takes up glucose but permits accumulation of triglyceride in the cells. Thus, after allowing insulin to act, the cells are ruptured and triglyceride is quantitatively determined, whereby the degree of the action of insulin and the degree of sensitivity can be known.

As is evident from the above-mentioned test results, the inventive compounds significantly increased the insulin sensitivity of 3T3-L1 cells.

The pharmacological activity of compound (I') was tested as follows.

EXPERIMENTAL EXAMPLE 2

Evaluation of Serum Glucose of Diabetic Mice

Genetically obese, hyperglycemic, hyperinsulinemic and hyperlipidemic diabetic mice (KK-Ay, male, Clea Japan, Inc., 8 weeks of age) were used for the pharmacological tests. Before the initiation of the drug administration, about 100 μl of blood was taken from orbital venosus under light ether anesthesia, and serum glucose was measured as described below. Based on the obtained value and body weight, the mice were grouped (6 per group) in such a manner that there existed no differences between the groups.

The test compounds were those of Examples 1 and 5 and Reference Example 1, as well as the above-mentioned control compound.

The test compounds were respectively dissolved in ethanol (three levels of concentrations per compound) and added to a powdered diet (CRF-1, ORIENTAL YEAST CO., LTD.). The diet was homogeneously mixed and ethanol was evaporated. The diet was given to the above-mentioned mice for 4 days, and the test compounds were orally administered (3 doses each). To a control group, CRF-1 powdered diet was given.

At day 4, blood samples (ca. 200 μl) were taken again in the same manner as above, and serum was separated (12,000 rpm, 5 min.) and used for the determination. Serum glucose was measured by hexokinase method (LYQUITECH glucose-HK-test; Boehlinger Marnheim Yamanouchi). Used for the determination was an automatic analyzer COBAS FARA II (Roche).

Changes in percentage of serum glucose of each group were calculated as follows from the values obtained at day 4 from the control group and the group administered with test compounds.

$$\text{Change in percentage of serum glucose (\%)} = \frac{[(\text{serum glucose of each group}) - (\text{serum glucose of control group})]}{(\text{serum glucose of control group})} \times 100$$

The changes in percentage of serum glucose was plotted on the axis of ordinates and the dose (mg/kg/day) of the test compound was plotted on the axis of abscissa (log), and the dose corresponding to a −50% change was read and taken as the ED50 of each test compound.

The results are shown in Table 2.

TABLE 2

| Test compound | Serum glucose ED50 (mg/kg/day) |
|---|---|
| Example 1 | 0.12 |
| Example 5 | 2.70 |
| Ref. Ex. 1 | 0.17 |
| Control compound | 10.6 |

As shown in Table 2, the compounds of the present invention significantly lowered serum glucose of diabetic mice.

INDUSTRIAL APPLICABILITY

The compound and a salt thereof of the present invention have extremely potent and less toxic hypoglycemic action as compared to known compounds and other therapeutic agents of diabetes, and are very useful as therapeutic agents for diabetes and hyperlipidemia. In addition, the pharmaceutical composition of the present invention is expected to be useful for the prevention of the complications of diabetes, especially for the prevention of arteriosclerosis.

This application is based on application No. 217548/1996 filed in Japan, the content of which is incorporated hereinto by reference.

What is claimed is:

1. A novel propionic acid derivative of the formula (I):

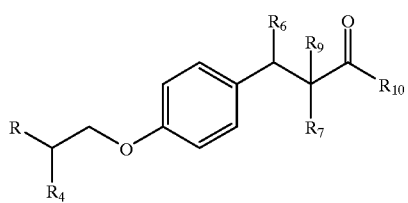

wherein R is a group of the formula:

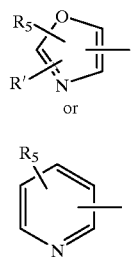

wherein
R' is an optionally substituted aromatic hydrocarbon, an optionally substituted alicyclic hydrocarbon, an optionally substituted heterocyclic group or an optionally substituted fused heterocyclic group, and
$R_5$ is a lower alkyl;
$R_4$ is a hydrogen atom or a lower alkyl;
$R_6$ is a hydrogen atom;
$R_7$ is carboxy, an acyl, an optionally substituted alkoxycarbonyl, an optionally substituted lower alkyl, an optionally substituted carbamoyl, an optionally substituted aryloxycarbonyl, or an optionally substituted aralkyloxycarbonyl;
$R_9$ is a hydrogen atom, an optionally substituted lower alkyl or an optionally substituted alkoxycarbonyl; and
$R_{10}$ is a hydroxy, an optionally substituted amino, an optionally substituted lower alkoxy, an optionally substituted lower alkyl, an optionally substituted aryloxy, or an optionally substituted aralkyloxy;
provided that when $R_7$ is an alkoxycarbonyl and $R_9$ is a hydrogen atom, $R_{10}$ is not a lower alkoxy,
or a pharmaceutically acceptable salt thereof.

2. The novel propionic acid derivative of claim 1, having the formula (I):

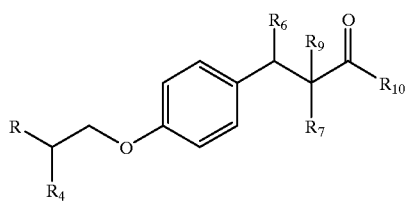

wherein
R is a group of the formula:

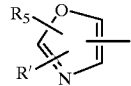

wherein
R' is an aromatic hydrocarbon or a fused heterocyclic group, and
$R_5$ is a lower alkyl;
$R_4$ is a hydrogen atom;
$R_6$ is a hydrogen atom;
$R_7$ is carboxy, an acyl, an optionally substituted alkoxycarbonyl, a lower alkyl substituted by alkoxycarbonyl, a lower alkyl, a carbamoyl, a carbamoyl optionally substituded by alkoxyalkyl or acyl, an aryloxycarbonyl, or an aralkyloxycarbonyl;
$R_9$ is a hydrogen atom or a lower alkyl optionally substituted by alkoxycarbonyl; and
$R_{10}$ is a hydroxy, an amino optionally substituted by lower alkyl, a lower alkoxy, a lower alkyl, an aryloxy or an aralkyloxy,
provided that when $R_7$ is an alkoxycarbonyl and $R_9$ is a hydrogen atom, $R_{10}$ is not a lower alkoxy,
or a pharmaceutically acceptable salt thereof.

3. The novel propionic acid derivative of claim 1, which is a member selected from the group consisting of:
2-methoxycarbonyl-3-[4-[2-(5-methyl-2-phenyl-4-oxazolyl)ethoxy]phenyl]propionic acid,
methyl 2-carbamoyl-3-[4-[2-(5-methyl-2-phenyl-4-oxazolyl)ethoxy]phenyl]propionate,
2-[4-[2-(5-methyl-2-phenyl-4-oxazolyl)ethoxy]benzyl]malonic acid,
methyl 2-methoxycarbonylcarbamoyl-3-[4-[2-(5-methyl-2-phenyl-4-oxazolyl)ethoxy]phenyl]propionate,
2-methoxycarbonyl-2-methyl-3-[4-[2-(5-methyl-2-phenyl-4-oxazolyl)ethoxy]phenyl]propionic acid,
methyl 2-carbamoyl-2-methyl-3-[4-[2-(5-methyl-2-phenyl-4-oxazolyl)ethoxy]phenyl]propionate,
2-carbamoyl-2-methyl-3-[4-[2-(5-methyl-2-phenyl-4-oxazolyl)ethoxy]phenyl]propionic acid and
2-benzyloxycarbonyl-3-[4-[2-(5-methyl-2-phenyl-4-oxazolyl)ethoxy]phenyl]propionic acid,
or a pharmaceutically acceptable salt thereof.

4. A pharmaceutical composition comprising a propionic acid derivative of formula (I) as claimed in claim 1 and a pharmacologically acceptable carrier.

5. The pharmaceutical composition of claim 4, comprising a propionic acid derivative of formula (I):

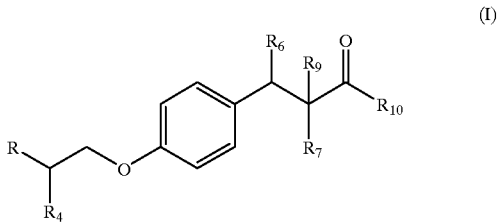

wherein
R is a group of the formula:

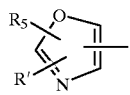

wherein
R' is an aromatic hydrocarbon or a fused heterocyclic group, and
$R_5$ is a lower alkyl;
$R_4$ is a hydrogen atom;
$R_6$ is a hydrogen atom;
$R_7$ is carboxy, an acyl, an optionally substituted alkoxycarbonyl, a lower alkyl substituted by alkoxycarbonyl, a lower alkyl, a carbamoyl, a carbamoyl optionally substituded by alkoxyalkyl or acyl, an aryloxycarbonyl, or an aralkyloxycarbonyl;
$R_9$ is a hydrogen atom or a lower alkyl optionally substituted by alkoxycarbonyl; and
$R_{10}$ is a hydroxy, an amino optionally substituted by lower alkyl, a lower alkoxy, a lower alkyl, an aryloxy or an aralkyloxy,
provided that when $R_7$ is an alkoxycarbonyl and $R_9$ is a hydrogen atom, $R_{10}$ is not a lower alkoxy,
or a pharmaceutically acceptable salt thereof and a pharmacologically acceptable carrier.

6. The pharmaceutical composition of claim 4 comprising a propionic acid derivative selected from the group consisting of:

2-methoxycarbonyl-3-[4-[2-(5-methyl-2-phenyl-4-oxazolyl)ethoxy]phenyl]propionic acid, methyl 2-carbamoyl-3-[4-[2-(5-methyl-2-phenyl-4-oxazolyl)ethoxy]phenyl]propionate, 2-[4-[2-(5-methyl-2-phenyl-4-oxazolyl)ethoxy]benzyl]malonic acid, methyl 2-methoxycarbonylcarbamoyl-3-[4-[2-(5-methyl-2-phenyl-4-oxazolyl)ethoxy]phenyl]propionate, and 2-carbamoyl-2-methyl-3-[4-[2-(5-methyl-2-phenyl-4-oxazolyl)ethoxy]phenyl]propionic acid, or a pharmaceutically acceptable salt thereof and a pharmacologically acceptable carrier.

7. A method of treating diabetes, comprising administering to a subject in need thereof, a pharmaceutical composition comprising a propionic derivative of formula (I) as claimed in claim 1.

* * * * *